(12) United States Patent
Rajagopal et al.

(10) Patent No.: US 10,820,991 B2
(45) Date of Patent: *Nov. 3, 2020

(54) TRANSCATHETER ATRIAL SEALING SKIRT, ANCHOR, AND TETHER AND METHODS OF IMPLANTATION

(71) Applicant: Opus Medical Therapies, LLC, Atlanta, GA (US)

(72) Inventors: Vivek Rajagopal, Atlanta, GA (US); Jaime Eduardo Sarabia, Mableton, GA (US); Yenchin Liao, Cary, NC (US)

(73) Assignee: OPUS MEDICAL THERAPIES, LLC, Atlanta, GA (US)

(*) Notice: Subject to any disclaimer, the term of this patent is extended or adjusted under 35 U.S.C. 154(b) by 202 days.

This patent is subject to a terminal disclaimer.

(21) Appl. No.: 15/943,792

(22) Filed: Apr. 3, 2018

(65) Prior Publication Data

US 2018/0289473 A1 Oct. 11, 2018

Related U.S. Application Data

(60) Provisional application No. 62/481,846, filed on Apr. 5, 2017, provisional application No. 62/509,587, filed
(Continued)

(51) Int. Cl.
A61F 2/24 (2006.01)

(52) U.S. Cl.
CPC ......... *A61F 2/2418* (2013.01); *A61F 2/2427* (2013.01); *A61F 2/2412* (2013.01);
(Continued)

(58) Field of Classification Search
CPC ..... A61F 2/24–2466; A61F 2220/0008; A61B 17/0401–0464; A61B 2017/2924; A61B 2017/291
See application file for complete search history.

(56) References Cited

U.S. PATENT DOCUMENTS

| 4,242,715 A | 12/1980 | Laird |
| 4,337,496 A | 6/1982 | Laird |

(Continued)

FOREIGN PATENT DOCUMENTS

| AU | 2016202264 A1 | 11/2016 |
| CA | 3 059 102 A1 | 10/2018 |

(Continued)

OTHER PUBLICATIONS

International Search Report and Written Opinion in corresponding International application No. PCT/US2018/025971 dated Jul. 10, 2018.
(Continued)

*Primary Examiner* — Tan-Uyen T Ho
*Assistant Examiner* — Charles M Wei
(74) *Attorney, Agent, or Firm* — FisherBroyles, LLP; Rachel H. Huffstetler

(57) ABSTRACT

A medical assembly and methods for endovascularly implanting a valve in the heart having a valve and an anchor assembly for positioning and restraining the valve. An anchor delivery system introduces and implants the anchor into the implantation site and a valve delivery system introduces and seals the valve at the deployment site. The present invention also relates to methods of implantation of the medical assembly and the valve.

22 Claims, 29 Drawing Sheets

Related U.S. Application Data on May 22, 2017, provisional application No. 62/558,315, filed on Sep. 13, 2017.

(52) U.S. Cl.
CPC ..... *A61F 2/2436* (2013.01); *A61F 2220/0016* (2013.01); *A61F 2220/0075* (2013.01); *A61F 2250/0004* (2013.01)

(56) References Cited

U.S. PATENT DOCUMENTS

| | | | |
|---|---|---|---|
| 4,746,057 A | 5/1988 | Wagner | |
| 4,830,360 A | 5/1989 | Carr, Jr. | |
| 5,079,776 A | 1/1992 | Crawford | |
| 5,312,438 A * | 5/1994 | Johnson | A61B 17/0401 606/104 |
| 5,683,451 A * | 11/1997 | Lenker | A61F 2/07 606/198 |
| 5,706,520 A | 1/1998 | Thornton et al. | |
| 6,093,162 A | 7/2000 | Fairleigh et al. | |
| 7,530,995 B2 | 5/2009 | Quijano et al. | |
| 7,780,725 B2 | 8/2010 | Salahieh et al. | |
| 8,147,542 B2 * | 4/2012 | Maisano | A61B 17/0401 623/2.11 |
| 8,236,049 B2 | 8/2012 | Rowe et al. | |
| 8,252,050 B2 * | 8/2012 | Maisano | A61B 17/0401 623/2.11 |
| 8,273,973 B2 | 9/2012 | Kimmons et al. | |
| 8,333,155 B2 | 12/2012 | Cylvick | |
| 8,403,983 B2 | 3/2013 | Quadri et al. | |
| 8,449,599 B2 | 5/2013 | Chau | |
| 8,489,165 B2 | 7/2013 | Segman | |
| 8,545,553 B2 * | 10/2013 | Zipory | A61B 17/0401 623/2.37 |
| 8,549,175 B2 | 10/2013 | Krishna | |
| 8,690,939 B2 * | 4/2014 | Miller | A61F 2/2457 623/2.11 |
| 8,728,155 B2 | 5/2014 | Montorfano et al. | |
| 8,790,394 B2 * | 7/2014 | Miller | A61B 17/0401 623/2.1 |
| 8,888,843 B2 | 11/2014 | Khairkhahan et al. | |
| 8,900,295 B2 * | 12/2014 | Migliazza | A61B 17/0401 623/2.19 |
| 8,932,348 B2 | 1/2015 | Solem et al. | |
| 8,998,976 B2 | 4/2015 | Gregg et al. | |
| 9,005,084 B2 | 4/2015 | Silagy et al. | |
| 9,033,383 B2 | 5/2015 | Rampersad | |
| 9,034,033 B2 * | 5/2015 | McLean | A61F 2/2427 623/2.12 |
| 9,078,749 B2 | 7/2015 | Lutter et al. | |
| 9,375,312 B2 | 6/2016 | Weber | |
| 9,439,763 B2 | 9/2016 | Geist et al. | |
| 9,441,832 B2 | 9/2016 | Bushee | |
| 9,474,605 B2 | 10/2016 | Rowe et al. | |
| 9,480,559 B2 * | 11/2016 | Vidlund | A61L 33/0011 |
| 9,486,306 B2 | 11/2016 | Tegels et al. | |
| 9,578,982 B2 | 2/2017 | Rampersad | |
| 9,827,092 B2 * | 11/2017 | Vidlund | A61B 17/0401 |
| 9,849,001 B2 | 12/2017 | Thompson, Jr. et al. | |
| 9,895,221 B2 | 2/2018 | Vidlund | |
| 9,986,993 B2 | 6/2018 | Vidlund et al. | |
| 10,039,639 B2 | 8/2018 | Tricares | |
| 2004/0190383 A1 | 9/2004 | Marcucelli et al. | |
| 2005/0137697 A1 * | 6/2005 | Salahieh | A61F 2/2418 623/2.11 |
| 2006/0235509 A1 * | 10/2006 | Lafontaine | A61F 2/2418 623/2.11 |
| 2006/0241656 A1 | 10/2006 | Starksen et al. | |
| 2006/0241745 A1 | 10/2006 | Solem | |
| 2007/0118151 A1 * | 5/2007 | Davidson | A61B 17/00234 606/144 |
| 2007/0277279 A1 | 12/2007 | Battat | |
| 2008/0125860 A1 | 5/2008 | Webler | |
| 2009/0276040 A1 * | 11/2009 | Rowe | A61B 17/0401 623/2.18 |
| 2010/0016655 A1 * | 1/2010 | Annest | A61B 17/00234 600/37 |
| 2011/0004296 A1 * | 1/2011 | Lutter | A61B 17/0401 623/1.26 |
| 2012/0078360 A1 | 3/2012 | Rafiee | |
| 2012/0136430 A1 | 5/2012 | Sochman et al. | |
| 2013/0023985 A1 * | 1/2013 | Khairkhahan | A61F 2/2466 623/2.38 |
| 2013/0116780 A1 | 5/2013 | Miller | |
| 2013/0172978 A1 * | 7/2013 | Vidlund | A61B 17/0401 623/1.12 |
| 2013/0184811 A1 * | 7/2013 | Rowe | A61F 2/2418 623/2.11 |
| 2013/0190861 A1 | 7/2013 | Chau et al. | |
| 2013/0211508 A1 | 8/2013 | Lane et al. | |
| 2013/0304197 A1 | 11/2013 | Buchbinder et al. | |
| 2013/0331929 A1 | 12/2013 | Mitra et al. | |
| 2014/0005778 A1 | 1/2014 | Buchbinder et al. | |
| 2014/0031928 A1 * | 1/2014 | Murphy | A61B 17/0057 623/2.18 |
| 2014/0163668 A1 | 6/2014 | Rafiee | |
| 2014/0296972 A1 | 10/2014 | Tegels et al. | |
| 2014/0316516 A1 | 10/2014 | Vidlund et al. | |
| 2014/0379076 A1 | 12/2014 | Vidlund et al. | |
| 2015/0142103 A1 | 5/2015 | Vidlund | |
| 2015/0250590 A1 | 9/2015 | Gries et al. | |
| 2015/0366666 A1 | 12/2015 | Khairkhahan et al. | |
| 2016/0022501 A1 | 1/2016 | Schultz et al. | |
| 2016/0120646 A1 | 5/2016 | Dwork et al. | |
| 2016/0213467 A1 | 7/2016 | Backus et al. | |
| 2016/0262878 A1 | 9/2016 | Backus et al. | |
| 2016/0262881 A1 * | 9/2016 | Schankereli | A61F 2/2436 |
| 2016/0310268 A1 * | 10/2016 | Oba | A61F 2/2436 |
| 2016/0317305 A1 | 11/2016 | Pelled et al. | |
| 2016/0324635 A1 | 11/2016 | Vidlund et al. | |
| 2016/0367360 A1 | 12/2016 | Cartledge et al. | |
| 2017/0143478 A1 | 5/2017 | Schwartz et al. | |
| 2017/0172737 A1 | 6/2017 | Kuetting et al. | |
| 2017/0209293 A1 | 7/2017 | Combs | |
| 2017/0227320 A1 | 8/2017 | Derousse | |
| 2017/0312078 A1 | 11/2017 | Krivoruchko | |
| 2018/0085215 A1 | 3/2018 | Vaturi et al. | |
| 2018/0289473 A1 * | 10/2018 | Rajagopal | A61F 2/2427 |
| 2018/0289474 A1 * | 10/2018 | Rajagopal | A61F 2/2418 |
| 2018/0289485 A1 * | 10/2018 | Rajagopal | A61F 2/2469 |
| 2018/0318071 A1 | 11/2018 | Lozonschi et al. | |
| 2019/0015205 A1 * | 1/2019 | Rajagopal | A61B 18/00 |
| 2020/0001135 A1 | 1/2020 | Rajagopal | |

FOREIGN PATENT DOCUMENTS

| | | |
|---|---|---|
| CA | 3 059 106 A1 | 10/2018 |
| CN | 103826750 A | 5/2014 |
| CN | 105658178 B | 6/2016 |
| CN | 106618798 A1 | 5/2017 |
| DE | 10 2012 002 785 A1 | 8/2013 |
| EP | 1 462 880 A2 | 9/2004 |
| EP | 1 462 880 A3 | 4/2005 |
| EP | 3311774 A1 | 4/2018 |
| KR | 10-2020-0007805 A | 1/2020 |
| KR | 10-2020-0007806 A | 1/2020 |
| UY | 37667 A | 10/2018 |
| UY | 37668 A | 10/2018 |
| WO | 1994/020049 A1 | 9/1994 |
| WO | 2005/094711 A2 | 10/2005 |
| WO | WO2014021905 A1 | 2/2014 |
| WO | 2016050751 A1 | 4/2016 |
| WO | 2016/179427 A1 | 11/2016 |
| WO | 2016186909 A1 | 11/2016 |
| WO | DM/098 100 S | 6/2017 |
| WO | 2017/117560 A1 | 7/2017 |
| WO | 2018/187390 A1 | 10/2018 |

(56) References Cited

FOREIGN PATENT DOCUMENTS

| | | | |
|---|---|---|---|
| WO | 2018/187495 | A1 | 10/2018 |
| WO | 2020/005527 | A1 | 1/2020 |

OTHER PUBLICATIONS

International Search Report and Written Opinion in corresponding International application No. PCT/PCT/US2018/026118 dated Jun. 15, 2018.

Toyama et al. Mitral annular motion in patients after transcatheter MitraClip and mitral valve surgery; Echocardiography 2017; 34: 334-339.

Boudjemline Y, Agnoletti G, Bonnet D, et al. Steps toward the percutaneous replacement of atrioventricular valves an experimental study. Journal of the American College of Cardiology 2005;46:360-5.

Bai Y, Chen HY, Zong GJ, et al. Percutaneous establishment of tricuspid regurgitation: an experimental model for transcatheter tricuspid valve replacement. Chinese medical journal 2010;123:806-9.

Laule M, Stangl V, Sanad W, Lembcke A, Baumann G, Stangl K. Percutaneous transfemoral management of severe secondary tricuspid regurgitation with Edwards Sapien XT bioprosthesis: first-in-man experience. Journal of the American College of Cardiology 2013;61:1929-31.

Lauten A, Doenst T, Hamadanchi A, Franz M, Figulla HR. Percutaneous bicaval valve implantation for transcatheter treatment of tricuspid regurgitation: clinical observations and 12-month follow-up. Circulation Cardiovascular Interventions 2014;7:268-72.

Lauten A, Ferrari M, Hekmat K, et al. Heterotopic transcatheter tricuspid valve implantation: first-in-man application of a novel approach to tricuspid regurgitation. European heart journal 2011;32:1207-13.

Lauten A, Figulla HR, Unbehaun A, et al. Interventional Treatment of Severe Tricuspid Regurgitation: Early Clinical Experience in a Multicenter, Observational, First-in-Man Study. Circulation Cardiovascular interventions 2018;11: e006061.

Lauten A, Figulla HR, Willich C, et al. Percutaneous caval stent valve implantation: investigation of an interventional approach for treatment of tricuspid regurgitation. European heart journal 2010;31:1274-81.

Lauten A, Laube A, Schubert H, et al. Transcatheter treatment of tricuspid regurgitation by caval valve implantation-experimental evaluation of decellularized tissue valves in central venous position. Catheterization and cardiovascular interventions : official journal of the Society for Cardiac Angiography & Interventions 2014.

Figulla HR, Kiss K, Lauten A. Transcatheter interventions for tricuspid regurgitation—heterotopic technology: TricValve. EuroIntervention : journal of EuroPCR in collaboration with the Working Group on Interventional Cardiology of the European Society of Cardiology 2016;12:Y116-8.

Barbanti M, Ye J, Pasupati S, El-Gamel A, Webb JG. The Helio transcatheter aortic dock for patients with aortic regurgitation. EuroIntervention : journal of EuroPCR in collaboration with the Working Group on Interventional Cardiology of the European Society of Cardiology 2013;9 Suppl:S91-4.

Hahn RT, Meduri CU, Davidson CJ, et al. Early Feasibility Study of a Transcatheter Tricuspid Valve Annuloplasty: SCOUT Trial 30-Day Results. Journal of the American College of Cardiology 2017;69:1795-806.

Rosser BA, Taramasso M, Maisano F. Transcatheter interventions for tricuspid regurgitation: TriCinch (4Tech). EuroIntervention : journal of EuroPCR in collaboration with the Working Group on Interventional Cardiology of the European Society of Cardiology 2016;12:Y110-2.

Stephan von Bardeleben R, Tamm A, Emrich T, Munzel T, Schulz E. Percutaneous transvenous direct annuloplasty of a human tricuspid valve using the Valtech Cardioband. European heart journal 2017;38:690.

Kuwata S, Taramasso M, Nietlispach F, Maisano F. Transcatheter tricuspid valve repair toward a surgical standard: first-in-man report of direct annuloplasty with a cardioband device to treat severe functional tricuspid regurgitation. European heart journal 2017.

Rogers J. Transcatheter TR solution 6: Millipede. Transcatheter Cardiovascular Therapeutics; 2017 Nov. 1, 2017; Denver, Colorado.

Parada-Campelo F, Perlman G, Philippon F, et al. First-in-Man Experience of a Novel Transcatheter Repair System for Treating Severe Tricuspid Regurgitation Journal of the American College of Cardiology 2015;66:2475-83.

Nickenig G, Kowalski M, Hausleiter J, et al. Transcatheter Treatment of Severe Tricuspid Regurgitation With the Edge-to-Edge MitraClip Technique. Circulation 2017;135:1802-14.

Cao R Catheter-Based Tricuspid Valve Replacement Via Right Atrium: An Animal Experimental Study. Transcatheter Cardiovascular Therapeutics; 2017; Denver, Colorado.

Navia JL, Kapadia S, Elgharably H, et al. First-in-Human Implantations of the NaviGate Bioprosthesis in a Severely Dilated Tricuspid Annulus and in a Failed Tricuspid Annuloplasty Ring. Circulation Cardiovascular interventions 2017;10.

Regueiro, et al. Transcatheter Mitral Valve Replacement: Insights From Early Clinical Experience and Future Challenges; JACC vol. 69, No. 17, 2017; May 2, 2017: 2175-92.

International Search Report and Written Opinion of the International Searching Authority dated Aug. 30, 2019, in International Application No. PCT/US19/36428.

Non-Final Office Action received for U.S. Appl. No. 15/943,971 dated Jan. 8, 2020, 49 pages.

International Search Report and Written Opinion issued in corresponding International Application No. PCT/US2019/057145 dated Dec. 31, 2019.

International Preliminary Report on Patentability received for PCT Application Serial No. PCT/US2018/025971 dated Oct. 17, 2019, 9 pages.

International Preliminary Report on Patentability received for PCT Application Serial No. PCT/US2018/026118 dated Oct. 17, 2019, 11 pages.

* cited by examiner

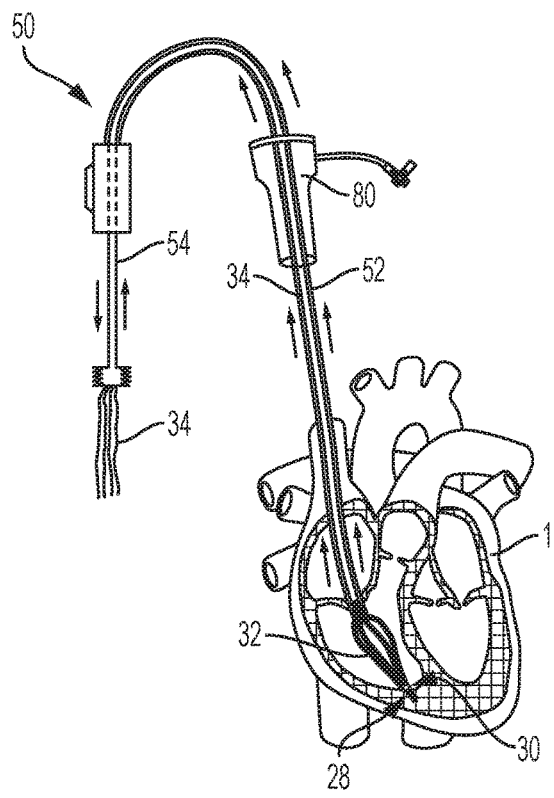
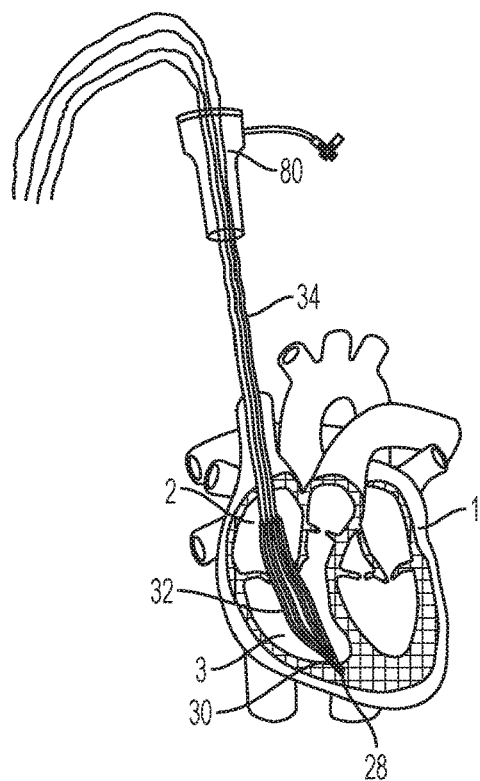
Figure 5A
Figure 5B
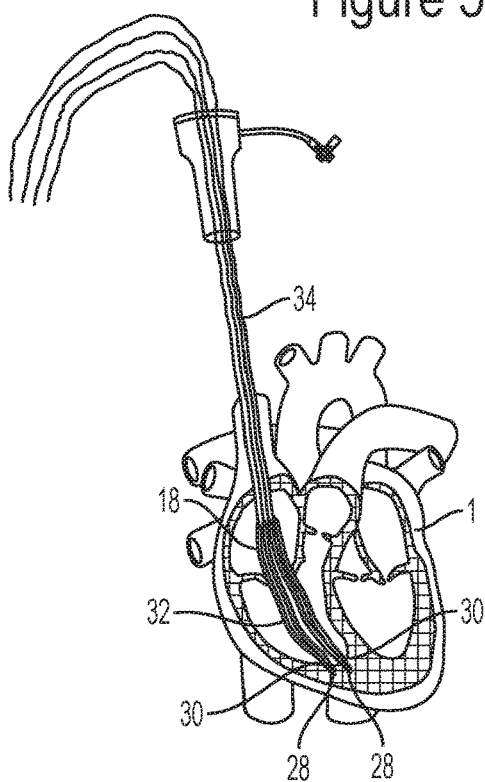
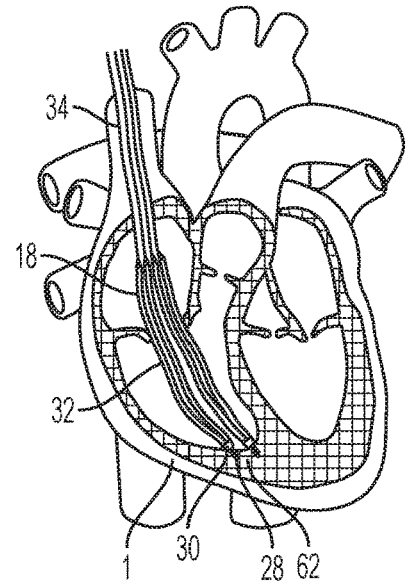
Figure 6A
Figure 6B

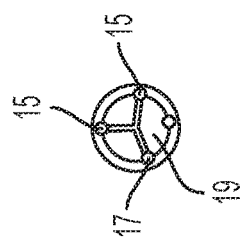
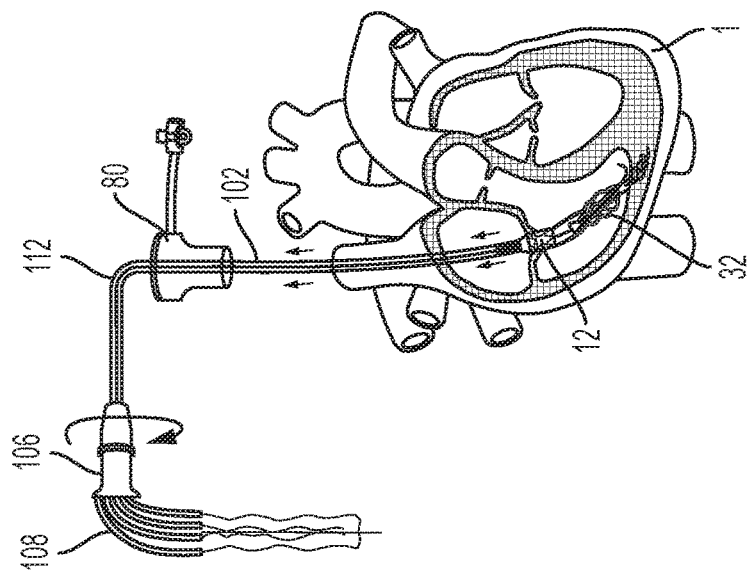
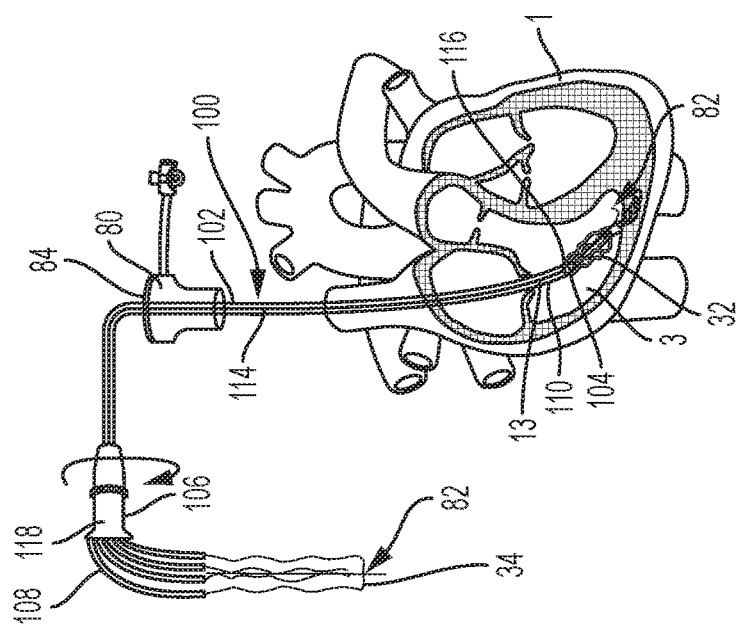

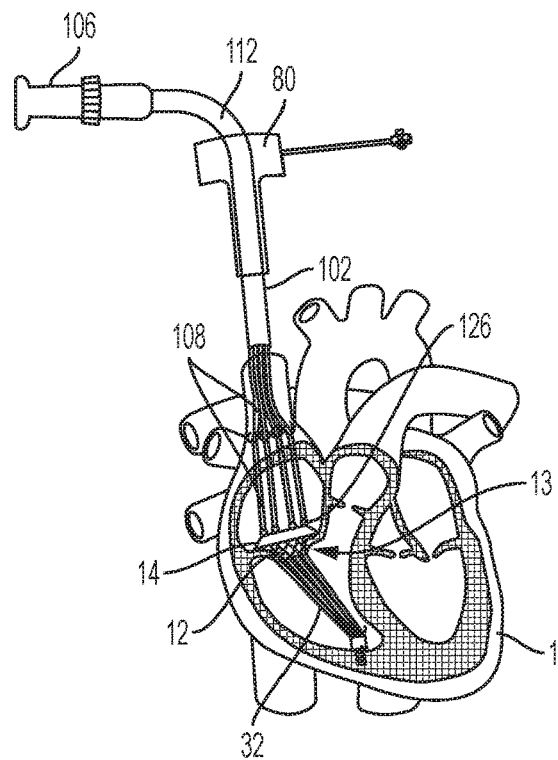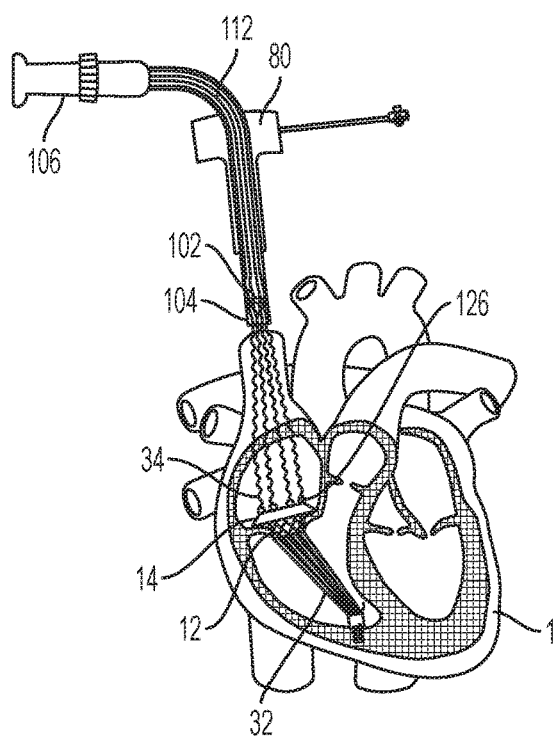
Figure 9A
Figure 9B
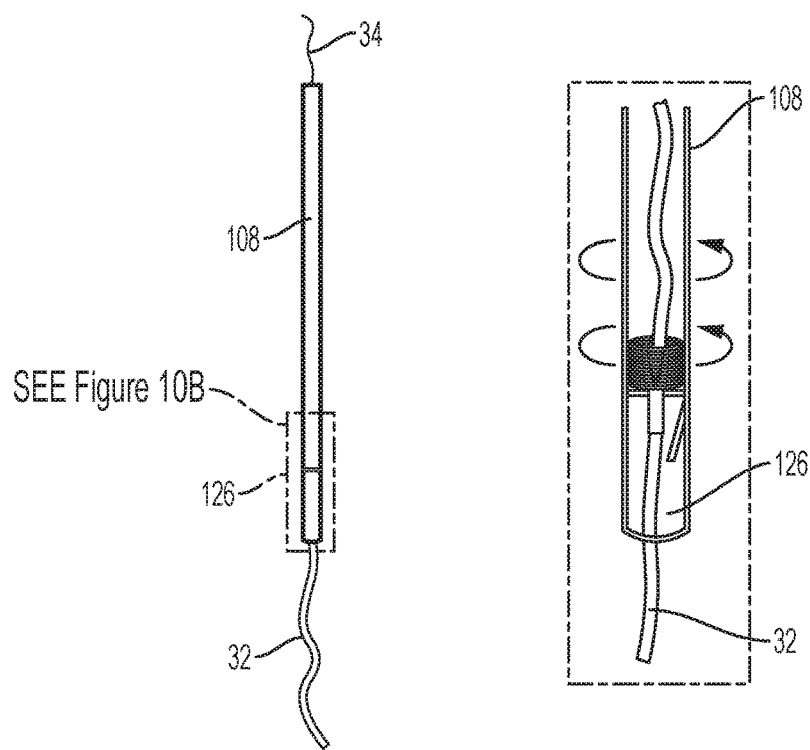
Figure 10A
Figure 10B

Figure 11A - D

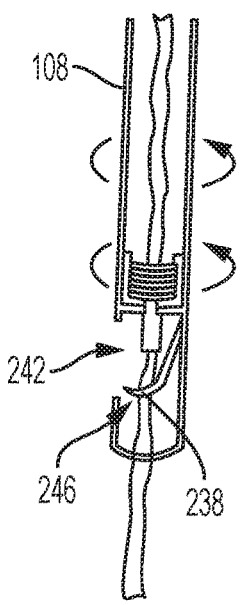
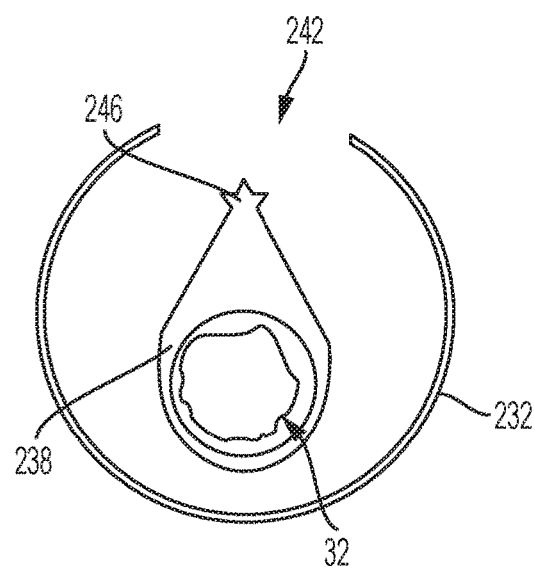
Figure 13A                    Figure 13B
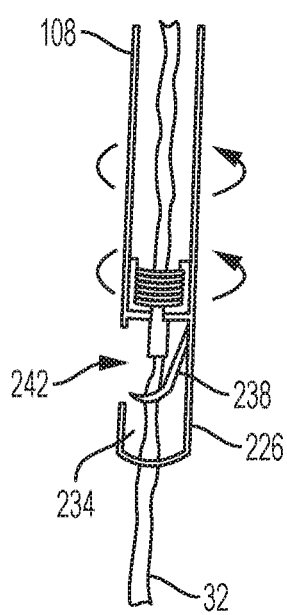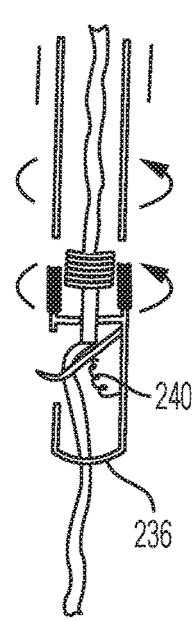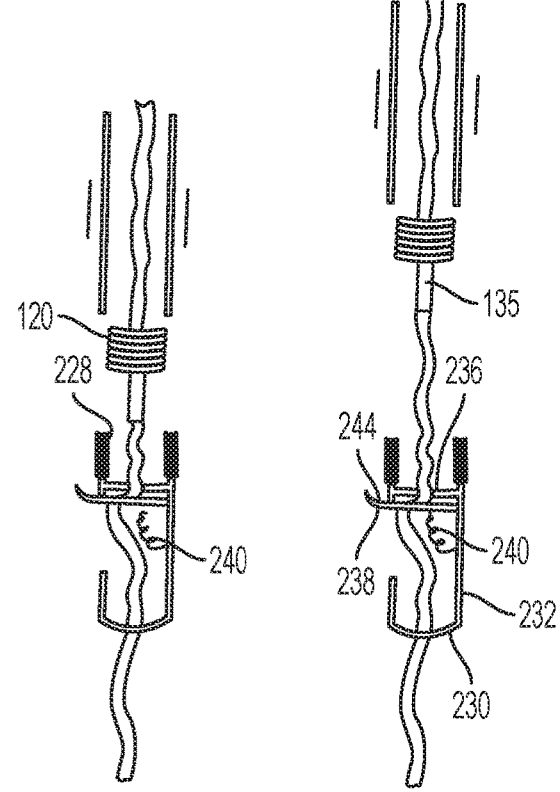
Figure 14A - D

TRANSCATHETER ATRIAL SEALING SKIRT, ANCHOR, AND TETHER AND METHODS OF IMPLANTATION

CROSS REFERENCE TO RELATED APPLICATIONS

The application is a claims priority to Provisional Patent Application Ser. Nos. 62/481,846 (filed Apr. 5, 2017), 62/509,587 (filed May 22, 2017), and 62/558,315 (filed Sep. 13, 2017), the disclosures of all are herein incorporated by reference.

FIELD OF THE INVENTION

The present invention relates generally to a medical assembly for minimally invasively implanting a valve in the heart, a novel valve for replacing the native heart valve, and an anchor system for positioning and restraining the valve. The present invention also relates to methods of implantation of components of the medical assembly and the valve. More specifically, the invention pertains to a novel transcatheter valve, transcatheter valve skirt, tether and anchor, anchor delivery system, and a valve delivery device as well as methods related to such assembly for endovascularly implanting the valve across the tricuspid valve, for replacing the function of the native tricuspid valve.

BACKGROUND OF THE INVENTION

Transcatheter valves have proven safe and effective for the replacement of native cardiac valves. Although tested extensively for replacement of aortic, mitral, and pulmonic valves, less experience exists for replacement of tricuspid valves given the complex and delicate anatomy to which prostheses must anchor. Also, anchoring either in the in-situ position of cardiac valves or in other body lumens remains challenging given great heterogeneity in shapes and sizes of either cardiac valve annuli or other lumens. In this regard, treatment of tricuspid valve regurgitation remains the most challenging, and fewer transcatheter treatments have been developed.

Tricuspid valve disease, primarily tricuspid regurgitation (TR), results from either a primary degeneration of the valve (e.g. endocarditis, rheumatic disease, carcinoid, congenital disease, drugs, perforation from intracardiac leads, or other causes), or more commonly from tricuspid annular dilation, secondary to either right atrial and/or right ventricular dilation. TR causes right atrial volume overload, which congests the superior vena cava (SVC) and inferior vena cava (IVC). Congestion of SVC causes plethora of the upper body, and congestion of the IVC causes hepatic/renal congestion, leading to signs and symptoms of congestive heart failure, namely peripheral edema, ascites, dyspnea on exertion and other symptoms. Additionally, persistent right heart volume overload from TR leads to progressive right ventricular dilation and failure, increasing mortality. Because patients suffering TR typically have high surgical risk, developing minimally invasive transcatheter methods to treat TR can be important.

In 2005, Boudjemline et al developed a novel stent valve, and placed it in the tricuspid annulus of eight sheep. In one animal the valve was trapped in tricuspid cordae, and in another animal the valve had significant paravalvular regurgitation, raising concerns about this approach. No further development of the valve occurred. In 2008, Bai et al. tested a similar type of stent valve, implanting it into the tricuspid annulus of ten sheep. Two animals died during the procedure; despite sustained function of the valve in surviving sheep up to six months, no further development of this valve has continued.

Because of these challenges of anchoring a valve in the tricuspid annulus, Lauten et al in 2010 designed and implanted stent valves in the IVC and SVC of a sheep model of severe TR, thereby minimizing the transmission of tricuspid regurgitant volume through the vena cava to organs. They demonstrated decreased pressure in the IVC and increased cardiac output.

Lauten and Laule in 2011 and 2013, respectively, implanted similar custom-made self-expanding stents in the vena cava of patients suffering from severe TR, and both patients had sustained reductions in vena caval pressures and clinical improvement at 12 months.

U.S. Pat. No. 7,530,995 describes a device, analogous to above method, that reduces pressure effects of TR by placing a stented tissue valve in the SVC, secured via at least one elongate connecting member, to a second stented tissue valve in the IVC. U.S. Pat. Pub. No. US 2012/0136430 A1 details a similar device, consisting of two caval stents, connected by a bridge, with two conical valves movable along the bridge to adjust the distance between the valves.

Laule et al. further simplified the implantation of valves in the vena cava by using a commercially available transcatheter valve, the Sapien XT (Edwards LifeSciences, Irvine, Calif.), in the cava of three patients, using self-expanding stents as landing zones.

The methods detailed in sections [0006-0009] suffer several limitations. Lauten's and Laule's techniques, along with the devices described in [0008] require customization to each patient, leading to biological valves with a broad range in size. Inherently, such as broad range in size results in uncertain durability and function, and limits widespread application given need for individual customization. Laule's technique of using a commercially available transcatheter valve, the Sapien valve (with its known performance and durability in thousands of patients), partially solves this, but is limited by seating difficulties and paravalvular regurgitation that would result from implantation in SVCs or IVCs bigger than the largest Sapien valve—29 mm, which occurs commonly in patients with TR. Similarly, other currently available valves cannot work in SVC/IVC diameters bigger than 30-31 mm.

To solve this, Lauten and colleagues have developed an SVC and IVC self-expanding prosthesis, the Tric Valve (Vertriebs GmbH, Germany), which solves some of the sizing and customization problems outlined in section [0007].

Nonetheless, the caval valve solutions outlined in [0006-0009 and 0011] suffer this same limitation; specifically, IVC and/or SVC stent valves do not completely restore the function of the tricuspid valve because they are not placed in the anatomically correct position—across the tricuspid annulus. Hence, they palliate symptoms but do not fundamentally address right ventricle (RV) volume overload caused by TR. To address volume overload, intra-annular anchoring of a valve across the native tricuspid valve is required; the above techniques are not suitable for intra-annular anchoring of transcatheter valves given the fragile and complex paraboloid annular anatomy of the tricuspid annulus, along with large and flared anchoring zones in the atria and ventricles connected to the annuli.

Although investigators have developed docking systems to aid in intra-annular anchoring of transcatheter valves, these techniques are less likely to work for the tricuspid valve for several reasons. For example, Barbanti and colleagues have tested the Helio transcatheter aortic dock (Edwards LifeSciences, Irvine, Calif.), a self-expanding stent covered with expanded polytetrafluoroethylene (ePTFE), to serve as a platform across a severely regurgitant aortic valve to anchor a Sapien transcatheter aortic valve. Although effective in this location, this platform would not remain anchored in a tricuspid annulus; unlike the aortic annulus, the tricuspid annulus has a complex paraboloid shape, easy distensibility, and lack of calcium, which could preclude the Helio dock, a simple tubular structure, from remaining in place.

Buchbinder and colleagues developed a docking system to anchor transcatheter aortic valves in the mitral position. They describe a docking system consisting of one or two self-expandable or balloon expandable rings, composed of rigid and semi-rigid materials, for intra-atrial and/or intra-ventricular stabilization, with bridging members that connect the rings and lock the transcatheter valve into place. The mitral valve annulus, flanked by thick fibrous trigones and in continuity with the thick left ventricular myocardium, has the external support to accommodate expandable rigid and semi-rigid materials.

Conversely, approximately three-quarters of the tricuspid valve annulus has minimal external support and is connected to the thin-walled and distensible right atrium and right ventricle. Given the fragility of this annulus, any metal docking system, even while using a compliant metal such as Nitinol, has a higher risk of erosion around the tricuspid annulus than any other valvular annulus. Moreover, any rigid or semi-rigid anchoring device is likely to have malposition over time given that any tricuspid annulus can dilate over the course of weeks.

To address tricuspid annular dilatation, several transcatheter approaches have been performed to reduce annular dimensions, allowing better tricuspid valve coaptation with reduction in TR. Investigators in the SCOUT I trial describe using the Mitralign system (Mitralign Inc., Tewksbury, Mass., USA) to place pledgeted sutures via a trans-jugular transvenous approach into the tricuspid annulus, thereby shrinking the annular dimensions. Similarly, the TriCinch device (4Tech, Galway, Ireland) reduces the annular dimensions by a screw in the annulus that is tensioned to a stent in the IVC. Mimicking a surgical ring, the Cardioband device (Valtech, Edwards LifeScience, Irving, Calif.) is a semi-complete annuloplasty ring that can be delivered and fixed to the tricuspid annulus minimally invasively. In the same way, the Millipede device (Boston Scientific, Marlborough, Mass.) mimics a complete surgical annuloplasty ring and can be delivered minimally invasively.

Nonetheless, these approaches have limitations. The Mitralign system has a steep learning curve, often leaving residual moderate to severe TR, does not fix leaflet abnormalities, and is less effective in presence of intracardiac leads. Moreover, any further RV remodeling with leaflet tethering would cause recurrent TR despite annular reduction. The same limitations apply to the TriCinch device, which also has the downside of requiring a stent in the IVC. Although the Cardioband device provides more complete annular reduction, it also leaves moderate to severe TR, and is less effective in the presence of leaflet abnormalities or intracardiac leads. Finally, the Millipede device, with its complete ring, provides the greatest annular reduction, but once again does not address leaflet abnormalities or intracardiac leads.

Other transcatheter approaches address TR by facilitating leaflet coaptation through direct device interaction with the leaflets. Parada-Campello and colleagues described their initial experience with the Forma Repair System (Edwards Lifesciences, Irvine, Calif.). This device consists of a foam-filled polymer balloon that is positioned over an RV anchor, allowing the tricuspid leaflets to coapt against the spacer, given the leaflets functional competency, thereby reducing TR. Another device, the MitraClip (Abbott Vascular, Abbott Park, Ill., USA), is used to plicate leaflets together.

Both devices, however, suffer significant limitations. The Forma Repair system has a fixed size balloon, and any further annular dilatation and/or leaflet tethering after implantation leads to recurrent TR. Furthermore, initial human experience has demonstrated a high major adverse event rate, including anchor dislodgement, pericardial tamponade, and emergent cardiac surgery. Tricuspid clipping with the MitraClip system is technically demanding with uncertain reproducibility, and moderate to severe residual TR is common. Like annuloplasty techniques, the Forma Repair system and the MitraClip cannot treat TR effectively in the presence of significant leaflet abnormalities or pacemaker leads.

In this regard, a transcatheter valve could solve the above problems, while minimizing risk of injury, if it could anchor without requiring leaflet or annulus fixation given the fragile tricuspid and right ventricular issue.

U.S. Patent Pub. No. US 2013/0172978 A1 describes a valve placed in the mitral position with an atrial skirt, intra-annular valve, and ventricular tether; this system does not require the annular or leaflet fixation that other transcatheter valves without tethers require. This valve, however, requires trans-apical access to the ventricle, which would be a very high-risk approach to the right ventricle. Also, the tether is fixed to the end of the valve. Thus, valve position is adjusted by pulling the tether through the trans-apical incision and securing it with an epicardial anchor, necessitating thoracotomy and access to the apex.

In contrast, the Lux valve (Ningbo Jenscare Biotechnology Co., LTD, Ningbo, China) is secured by a triangular paddle, fixed to the end of the valve, which anchors to the interventricular septum. Although the Lux valve showed stable anchoring in a goat, these animals had small, non-globular hearts (average tricuspid annular size ~2.5 cm, compared to ≥4 cm in humans). It is unclear how a fixed ventricular anchor will function in humans with severe TR, given the tremendous heterogeneity in basal/longitudinal remodeling of the right ventricle in these patients. Additionally, many TR patients suffer right ventricular dysfunction, and a fixed tether to the right ventricular myocardium could, via physical restraint or induction of scarring, further compromise right ventricular function.

The NaviGate valve (NaviGate Cardiac Structures, Inc., Lake Forest, Calif.) does not require a tether because it anchors directly to the native tricuspid valve using leaflet and annulus fixation. Although initial human experience has not demonstrated right atrial or ventricular injury, its anchoring mechanism to the leaflets and annulus prevents it from being repositionable or retrievable during the procedure, which are important safety features. Furthermore, NaviGate's annular anchoring mechanism requires a large valve, necessitating a very large delivery system, which limits truly percutaneous delivery to select patients. The large size of NaviGate also precludes it from being used as a docking system for commercially available transcatheter valves in the event of its structural deterioration. Finally, given that it requires full expansion against the annulus, it is unlikely this valve can be implanted in the presence of prior tricuspid leaflet clipping with the MitraClip, and is it likely this valve would damage any pre-existing intracardiac leads going across the tricuspid valve.

Accordingly, it remains desirable in the pertinent art to provide a transcatheter valve for placement across the tricuspid annulus that does not require annular anchoring, can be delivered without trans-apical access, is repositionable and retrievable, can function in the presence of any prior tricuspid repair, including tricuspid clips, can serve as a docking system for other transcatheter valves, and does not damage intracardiac leads.

SUMMARY

Presented herein is a medical assembly that is implanted minimally invasively across the tricuspid valve, for replacing the function of the native tricuspid valve. The method disclosed herein implants the tricuspid valve through a vein or vein-like anatomical structure including, but not limited to, either internal jugular, either subclavian vein or either femoral vein. Accordingly, and beneficially, no portion of the system requires surgical thoracotomy and trans-apical access for implantation.

In one aspect, the system comprises a transcatheter valve having an atrial sealing skirt configured to couple to and/or secure the valve to the atrial floor and at least one tether, with each tether attached to one anchor, configured to couple and/or secure the valve to an intracardiac wall, including but not limited to, the ventricular free wall, the ventricular apex, or the interventricular septum.

The valve is a self-expanding valve composed of nitinol and bovine, equine, or porcine pericardial leaflets, according to one aspect. In another aspect, the atrial sealing skirt is covered with a membrane having a diameter greater than the annulus at the site of deployment so that in use the membrane substantially covers the tricuspid annulus.

The medical assembly includes an anchor delivery system and a valve delivery system. The anchor delivery system introduces the anchor and attached tether, comprised of one or more cords, and secures the anchor. The valve delivery system provides for positioning of the valve and the sealing skirt thereon.

The at least one tether comprises at least one cord, with each cord fused to a suture, and the tether is connected to one anchor, comprised of an anchor cap and anchor screw, which is configured to be screwed into or otherwise securely attached to a portion of an intracardiac wall, such as the ventricular apex or interventricular septum. In one aspect, an anchor cap is coupled to the anchor screw, and at least one cord of the tether can extend from the anchor cap through the tricuspid annulus. The valve and the sealing skirt are threaded onto the cord so that the valve and the sealing skirt slidingly engage the cord. In another aspect, a suture is coupled to a proximal end of the cord and can extend outside of the heart to be accessible by a user.

The valve delivery system further comprises at least one atrial positioning rod having a distal end, an opposed proximal end and an inner rod lumen extending therebetween. A detachable lock is releasably coupled to the distal end of each positioning rod. A portion of the suture is inserted through the inner rod lumen and the positioning rod is advanced over the suture until the distal end of the rod is adjacent to the atrial sealing skirt. In one aspect, the positioning rod is used to position the skirt in a desired position. In another aspect, rotation of the positioning rod can cause the detachable lock to engage the cord to secure the cord to the sealing skirt in the desired position. Continued rotation of the positioning rod can detach the lock from the positioning rod and the rod is retracted from the heart.

Thus, the at least one cord of the tether couples the valve, via the anchor, to an intracardiac wall such as the ventricular apex or interventricular septum while the at least one detachable lock in the locked position prevents the proximal end of the cord from moving relative to the sealing skirt thereby securely fixing the valve in place in the tricuspid annulus.

Related methods of implantation are also provided. Other apparatuses, methods, systems, features, and advantages of the medical devices and systems that are implanted minimally invasively in the heart will be or become apparent to one with skill in the art upon examination of the following figures and detailed description. It is intended that all such additional apparatuses, methods, systems, features, and advantages be included within this description, be within the scope of the medical assembly that is implanted minimally invasively in the heart, and be protected by the accompanying claims.

DESCRIPTION OF THE FIGURES

FIG. 5A is a perspective view of the anchor delivery system of FIG. 3, in which the anchor delivery system is delivering a portion of the tether, connected to the anchor, of FIG. 2 into the right ventricle;

FIG. 5B is a perspective view of the tether, connected to the anchor, of FIG. 2 positioned in the right ventricle;

FIG. 6A is a perspective view of two tethers, each connected to an anchor of FIG. 2 positioned in a heart, according to one aspect;

FIG. 6B is a magnified view of the two tethers each connected to an anchor of FIG. 6A;

FIG. 7A is a perspective view of a valve delivery system of the transcatheter valve system of FIG. 1 according to one aspect, in which a portion of the valve delivery system is positioned in the right ventricle;

FIG. 7B is a perspective view of a valve of the transcatheter valve system of FIG. 1 according to one aspect, in which the valve is being positioned in a tricuspid annulus by the valve delivery system of FIG. 7A;

FIG. 7C is an end view of the valve of FIG. 7B;

FIG. 9A is a perspective view of a valve of the transcatheter valve system of FIG. 1, in which the valve is being locked into position in the tricuspid annulus by atrial locks;

FIG. 9B is a perspective view of a valve of the transcatheter valve system of FIG. 1, in which the valve is locked into position in the tricuspid annulus by atrial locks;

FIG. 10A is an elevational view of an atrial lock of the transcatheter valve system of FIG. 1, according to one aspect;

FIG. 10B is a magnified elevational view of the atrial lock of FIG. 10A;

FIGS. 11A-11D are progressive, elevational views illustrating the operation of the atrial lock of FIG. 10A;

FIG. 13A is an elevational view of the atrial lock of FIG. 12;

FIG. 13B is a cross-sectional view of the atrial lock of FIG. 13A.

FIGS. 14A-14D are progressive, elevational views illustrating the operation of the atrial lock of FIG. 12;

DESCRIPTION OF THE INVENTION

The present invention is understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes are made to the aspects described, while still obtaining the beneficial results of the present invention. It will also be apparent that some of the desired benefits of the present invention is obtained by selecting some of the features of the present invention without utilizing other features. Accordingly, those who work in the art will recognize that many modifications and adaptations to the present invention are possible and may even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "tether" includes aspects having two or more tethers unless the context clearly indicates otherwise.

Ranges is expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not. As used herein "fluid" refers to any substance that is free to flow and include liquids, gases, and plasma. "Fluid communication" as used herein refers to any connection or relative positioning permitting substances to freely flow between the relevant components.

Figure 1:
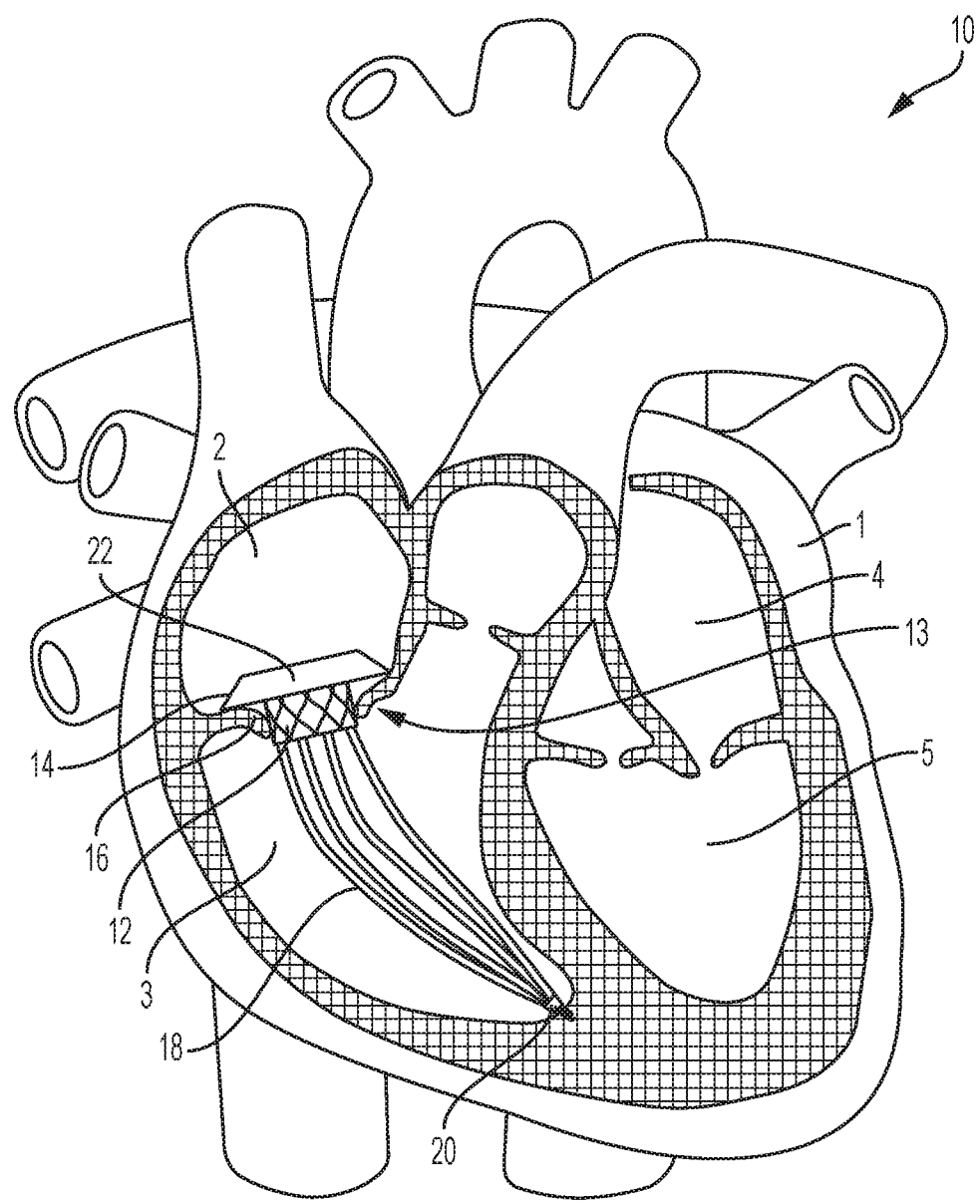
FIG. 1 is a cut-away perspective view of a heart showing the transcatheter valve system of the present application positioned in the heart, according to one aspect.

The disclosure herein relates to a medical assembly 10 for implanting a valve minimally invasively in the heart 1 and methods of implantation of portions of the assembly 10 to achieve replacement of the native heart valve. FIG. 1 illustrates the transcatheter valve 12 which has been implanted so as to replace the native tricuspid valve (for example) according to the method disclosed herein and with the medical assembly 10 disclosed herein. The assembly comprises a transcatheter valve 12 having an atrial sealing skirt 14 configured to couple to the atrial floor 16, and at least one tether 18 configured to connect the valve to at least one anchor 19 (FIG. 2), which affixes to an intracardiac wall such as the ventricular apex 20 as shown. The tether 18 may be anchored by anchor 19 to any intracardiac wall, including, but limited to, the interventricular septum, right ventricular apex, or right ventricular free wall. For the sake of discussion only, the ventricular apex 20 is shown but it is within the spirit and scope of the present invention to anchor the tether 18 to any intracardiac wall. The medical assembly 10 includes an anchor delivery system 50 (illustrated in FIGS. 3A and 3B) and a valve delivery assembly 100 (illustrated in FIG. 7A). The method for implanting the transcatheter tricuspid valve as herein shown and described includes, generally, the method of steps of: utilizing the anchor delivery system 50 to deliver the anchor and the tether to secure the anchor to an intracardiac wall such as the ventricular apex; removing the anchor delivery system 50; utilizing the valve delivery assembly 100 to position the valve and skirt; locking the atrial skirt; and removing the valve delivery assembly 100, thereby leaving the valve in place of the native tricuspid valve.

The Valve

The transcatheter valve 12 is sized and configured to replace the tricuspid valve between the right atrium 2 and right ventricle 3 as illustrated in FIG. 1. Optionally, however, with slight variations, the valve is sized and configured to be positioned in the mitral annulus between the left atrium 4 and the left ventricle 5. Accordingly, then, while referring primarily to tricuspid valve replacement devices, systems and methods, it is understood that with slight variations, these devices, systems and methods may be used to replace other valves, such as the mitral valve, the aortic valve, the pulmonary valve and the like. For the sake of discussion, only, the following description and attended drawings pertain to a tricuspid valve. With respect to the delivery assemblies and methods, these may be used and practiced with any appropriate valve replacement device. The disclosure herein is not limited to the valve shown and described.

As shown, the valve 12 is a self-expanding valve (that is, the valve is compressible so that it fits through a catheter of the assembly 10). In one aspect, the valve 12 is composed of nitinol and bovine, equine, or porcine pericardial leaflets 19, shown in FIG. 7C. In another aspect, the valve 12 has a valve diameter that is smaller than or approximately equal to the annulus at the site of deployment 13, such as the tricuspid annulus, thereby preventing or reducing apposition to the fragile tricuspid annulus. The valve 12 is operatively connected to at least one tether 18 including at least one cord 32 for securing the valve 12 within the heart as described below. At least one bore 15 is defined in the outer wall 17 of the valve 12, according to another aspect and as illustrated in FIG. 7C. Each bore 15 is sized and shaped so that a portion of cord of the tether passes through the bore 15. Thus, each cord 32 of the tether 18 is coupled to the valve without interfering with any leaflet 19 of the valve. In a further aspect, (not shown) the valve 12 may have anchoring elements positioned along its outer diameter. These anchoring elements allow additional fixation to tricuspid leaflets, but are not necessarily used as a primary fixation mechanism. Referring again to FIG. 1, an atrial sealing skirt 14 extends substantially circumferentially around the upper end of the transcatheter valve 12. The skirt 14 is covered with a membrane and has a diameter greater than the annulus at the site of deployment 13. For example, the sealing skirt 22 may have a skirt diameter greater than the diameter of the tricuspid annulus. In another aspect, the atrial skirt is formed by, but not limited to, synthetic materials from the classes consisting of polycarbonate, polyurethane, polyester, expanded polytetrafluoroethylene (ePTFE), polyethylene terephthalate (PET), silicone, natural or synthetic rubbers, or a combination thereof. The atrial skirt may also be covered with adult or juvenile bovine, ovine, equine, or porcine pericardium. Optionally, at least a portion of the atrial skirt 14 is formed from alternative materials, such as, for example and without limitation, polyurethane foam or saline-inflatable ring with the ability for polymer exchange for solidification of the ring.

In one aspect, the atrial sealing skirt 14 further comprises at least one atrial anchor 238 such as member protruding through an anchor exit port 242 allows stability in the atrium. Stability in the atrium thereby prevents retrograde migration of the valve 12, such as in the event of ventricular anchor dysfunction and the like.

Figure 15A:
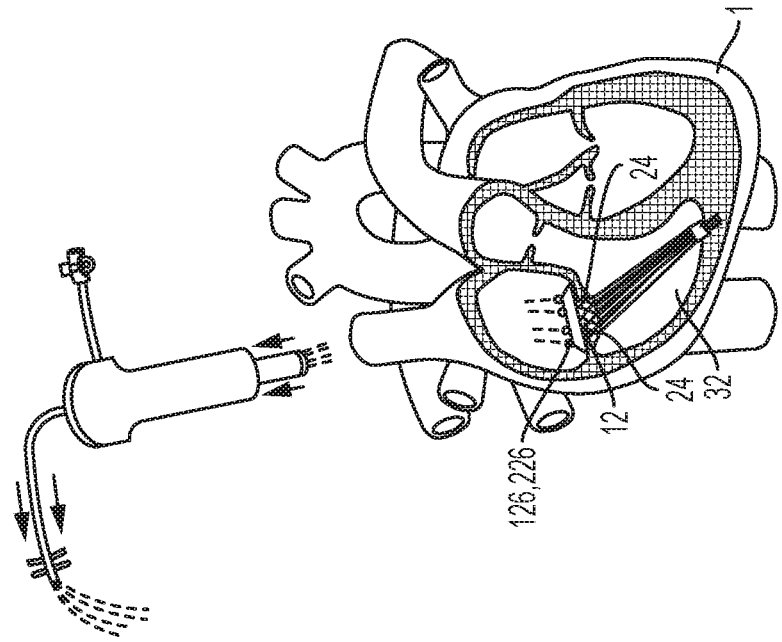
FIG. 15A is a perspective view of the transcatheter valve system of FIG. 1 positioned in the heart and with sutures remaining.
Figure 15B:
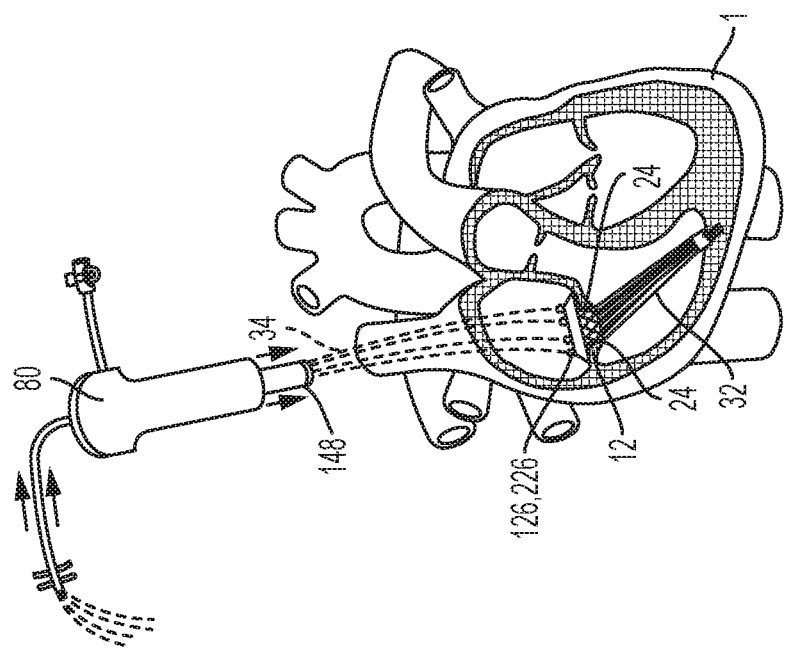
FIG. 15B is a perspective view of the transcatheter valve system of FIG. 1 positioned in the heart with all delivery devices retracted.

In another aspect, at least a portion of the atrial sealing skirt 14 has one or more fixation members 24, illustrated in FIG. 15B, positioned along its inferior edge, allowing further anchoring to the right atrial floor 16 and/or other portions on the atrial side of the tricuspid annulus, preventing migration of the valve 12 into the proximal right atrium 2, thereby preventing instability (e.g. rocking) and paravalvular regurgitation of prosthesis. Also, the atrial skirt 14 conforms to the atrial floor topography, including the ability to cover and seal intracardiac leads, such as permanent pacemaker leads. The ability of the atrial skirt 14 to seal over leads and prevent regurgitation around them distinguishes this transcatheter valve system from other transcatheter tricuspid repair systems.

The Tether and Anchor

Figure 2:
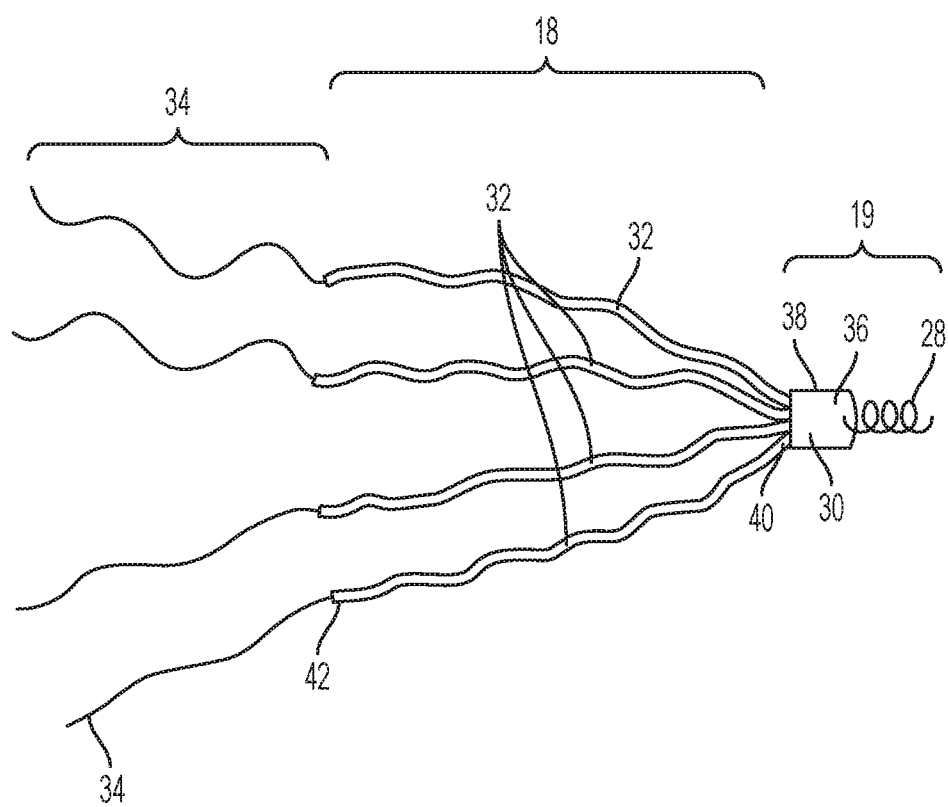
FIG. 2 is a side elevational view of a tether, with its cords fused to sutures, connected to an anchor of the transcatheter valve of FIG. 1, according to one aspect.

Referring now to FIG. 2, the at least one tether 18 is operatively connected to the replacement valve 12 and connects the valve 12 to the anchor 19. The tether 18 includes at least one cord 32, and each cord 32 is connected to a suture 34. The anchor 19 includes an anchor screw 28 and an anchor cap 30. In one aspect, the anchor screw is coupled to and extends from a distal end 36 of the anchor cap, and the at least one cord 32 of the tether 18 is coupled to and extends from a proximal end 38 of the anchor cap 30. That is, the anchor cap 30 is positioned between the anchor screw 28 and the cord 32. The anchor screw 28, of anchor 19, is configured to securely attach the tether 18 to an intracardiac wall such as the ventricular apex 20 of the heart 1. For example, the anchor screw 28 is an active fixation screw comprising threads or a coil that is securely rotated into the ventricular apex. The anchor via the anchor screw is configured to securely attach the tether to an intracardiac wall such as the ventricular apex 20 of the heart without extending through the apex and outside of the heart. Thus, in this aspect, substantially no portion of the assembly 10 completely penetrates and/or extends completely through any portion of the heart wall, and trans-apical access is not necessary. In a further aspect (not shown), rather than the anchor screw 28, a fixation mechanism composed of, but not limited to, nitinol, stainless steel, cobalt-chromium, or titanium alloys, in the shape of barbs, hooks, prongs and the like is positioned at the distal end 36 of the anchor cap 30 to securely attach the tether 18 to the ventricular apex 20 of the heart 1 without extending through the apex and outside of the heart.

The at least one cord 32 has a distal end 40 coupled to a portion of the anchor cap 30 and a proximal end 42 coupled to the suture 34. In one aspect, the cord is a strong yet flexible cord such as, for example and without limitation, an expanded polytetrafluoroethylene (ePTFE) or ultra-high-molecular-weight polyethylene (UHMWPE or UHMW) cord. In use, described more fully below, a central portion of the cord 32 (between the distal end and the proximal end) extends through and/or is coupled to the valve 12 to hold the valve in the desired position relative to the tricuspid annulus.

The Anchor Delivery System

Referring now to FIGS. 3A-3C, 4A and 4B, the anchor delivery system 50 for positioning and deploying the anchor cap 30 of anchor 19 at the desired position is illustrated. The delivery system 50 comprises an anchor delivery guide 52 and an anchor delivery rod 54. In this aspect, the anchor delivery guide 52 has a distal end 56, an opposed proximal end 58 and an inner guide lumen 57 extending between the anchor delivery guide tip 60 and the opposed proximal end 58, and is configured so that at least a portion of the anchor delivery rod 54 extends therethrough. In another aspect, at least a portion of the anchor delivery guide 52 is flexible so that a tip 60 at the distal end of the anchor delivery guide 52 is positioned at or adjacent to an intracardiac wall anchoring site 62 such as the ventricular apex 20.

The anchor delivery rod 54 is configured to securely attach the anchor screw 28 to the anchoring site 62. The anchor delivery rod 54 has a distal end 64, an opposed proximal end 66 and an inner rod lumen 59 extending therebetween, the inner rod lumen 59 is sized and configured so that at least a portion of the at least one tether 18 is inserted therethrough. In another aspect, at least a portion of the anchor delivery rod 54 is flexible so that a rod tip 68 at the distal end of the anchor delivery rod 54 is positioned at or adjacent the intracardiac wall anchoring site 62 such as the ventricular apex 20.

Figure 3A:
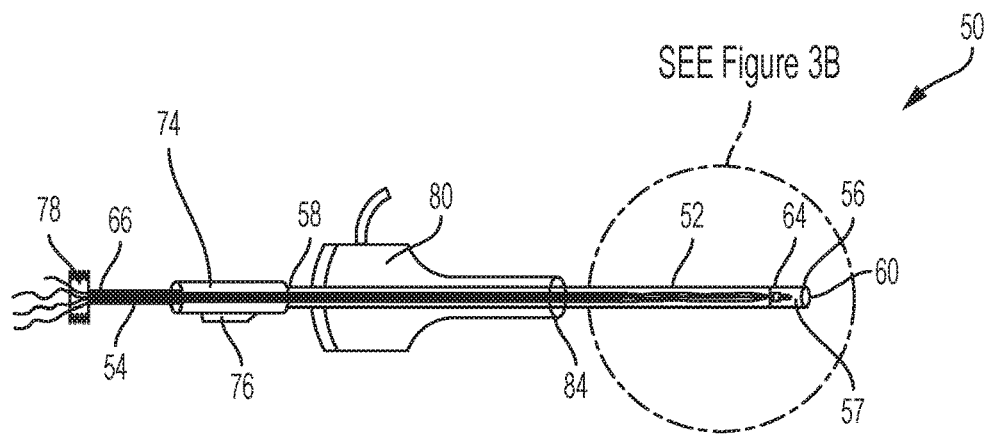
FIG. 3A is a side elevational view of an anchor delivery system of the transcatheter valve system of FIG. 1, according to one aspect.
Figure 3B:
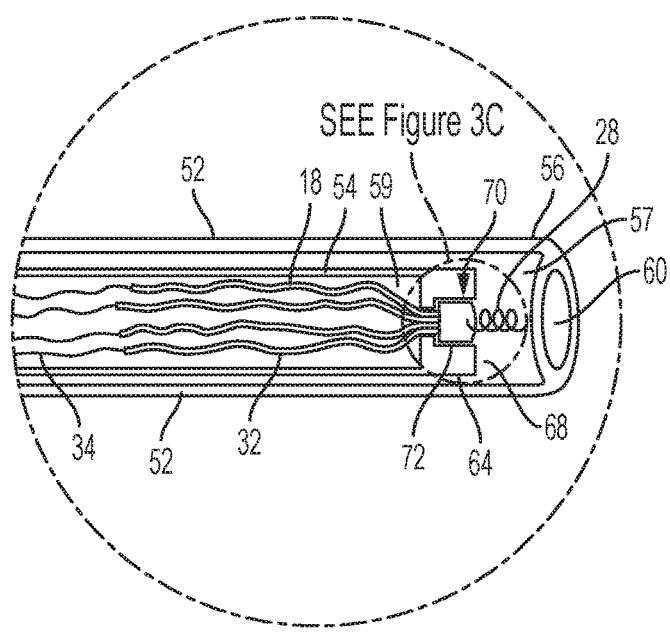
FIG. 3B is a magnified side elevational view of the anchor delivery system of FIG. 3A.
Figure 3C:
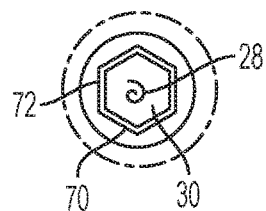
FIG. 3C is an end view of the anchor delivery system of FIG. 3A.

As shown in FIG. 3B, a bore or socket 70 is defined in the rod tip 68 of the anchor delivery rod 54. The socket is sized and configured to matingly engage the anchor cap 30. That is, at least a portion of the anchor cap is positioned in the socket 70 so that walls 72 of the socket engage the anchor cap. Thus, for example, when the anchor cap 30 is positioned in and engages the socket 70, rotation of the anchor delivery rod 54 rotates the anchor cap 30. Accordingly, the socket engages the anchor cap 30 and the anchor screw 28 extends distally from the anchor delivery rod 54 as illustrated in FIG. 3B. In a further aspect, when the socket 70 engages the anchor cap 30, the at least one cord 32 and at least a portion of the at least one suture 34 extends through the inner rod lumen of the anchor delivery rod 54.

The anchor delivery system 50 further comprises a guide handle 74 with a deflection knob 76 coupled to the anchor delivery guide 52. The guide handle and the deflection knob are configured and used to help guide the tip 60 of the anchor delivery guide to the intracardiac wall anchoring site 62 such as the ventricular apex 20. As shown in FIG. 3A, the anchor delivery system 50 includes a rod handle 78 coupled to the anchor delivery rod 54. In use, described more fully below, rotation of the rod handle 78 correspondingly rotates the rod tip 68 and the anchor cap 30 when the anchor cap 30 is received within the socket 70.

The anchor delivery system 50 includes a sheath 80 removably coupled to the anchor delivery guide 52. The sheath 80 is in fluid communication with the anchor delivery guide 52 so that fluids, such as carbon dioxide and the like surround the anchor delivery guide through the sheath. A central sheath channel 84 is defined by the sheath 80 that is in communication with the anchor delivery guide 52 so that the anchor delivery rod 54 and other system components extends through the central sheath channel 84.

The anchor delivery system 50 optionally includes a J-wire 82, as shown in FIGS. 7A, 7B, 8A and 8B that is guidable by the user to the anchoring site 62. The J-wire is, for example and without limitation, a 0.025" or 0.035" J-wire. Of course, J-wires having other diameters are contemplated. As in any over-the-wire system, the J-wire is introduced first via sheath 80 into the right atrium 3, across the site of deployment 13, into the right ventricle 3, to the anchoring site 62. By providing a pathway for the anchor delivery guide 52 to track over to its final target, a J-wire increases the efficiency and safety of this step.

The Anchor Delivery Method

Figure 4A:
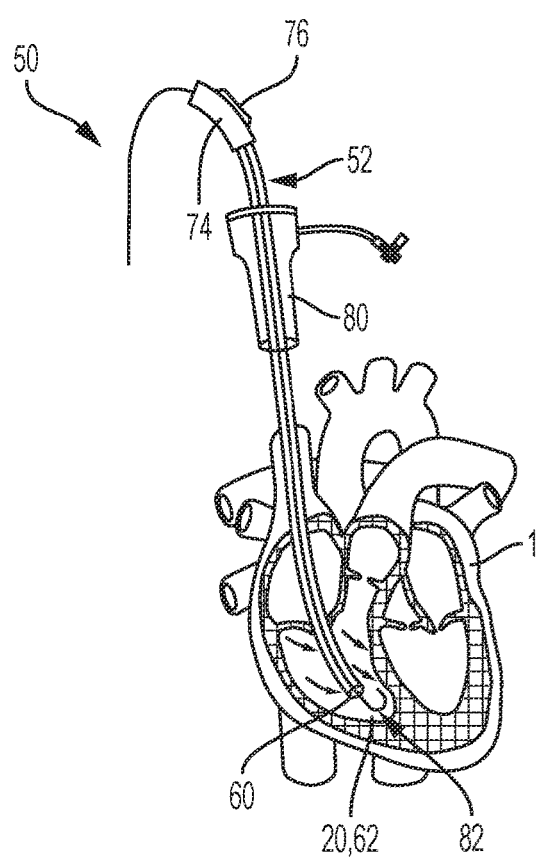
FIG. 4A is a perspective view of the anchor delivery system of FIG. 3, in which a portion of the device is positioned in the right ventricle.

To install the valve 12 in the tricuspid annulus, as shown in FIG. 4A, the J-wire 82, serving as a guidewire, is inserted into the right internal jugular vein, enters the right atrium and approaches the anchor implantation site 62. The anchor delivery system 50 is guided by the user, along the length of the previously implanted J-wire 82, to the intracardiac wall anchoring site 62 such as the ventricular apex 20. The anchor delivery guide tip 60 at the distal end 56 of the anchor delivery guide 52 is positioned at or adjacent the anchoring site such as the ventricular apex. As shown in FIG. 3A the, anchor delivery rod 54 and the tether 18, connected to the anchor cap 30 and anchor screw 28 of the anchor 19, are positioned within the inner guide lumen 57 of the anchor delivery guide 52. The anchor cap 30 is coupled to the distal end 64 of the anchor delivery rod 54 with the cord 32 of the tether 18 positioned in the lumen 59 of the anchor delivery rod 54. The anchor delivery rod 54 is advanced distally through the inner guide lumen of the anchor delivery guide 52 until the anchor cap 30 coupled to the distal end of the anchor delivery rod 54 is positioned at or adjacent the intracardiac wall anchoring site 62 such as the ventricular apex 20.

Figure 4B:
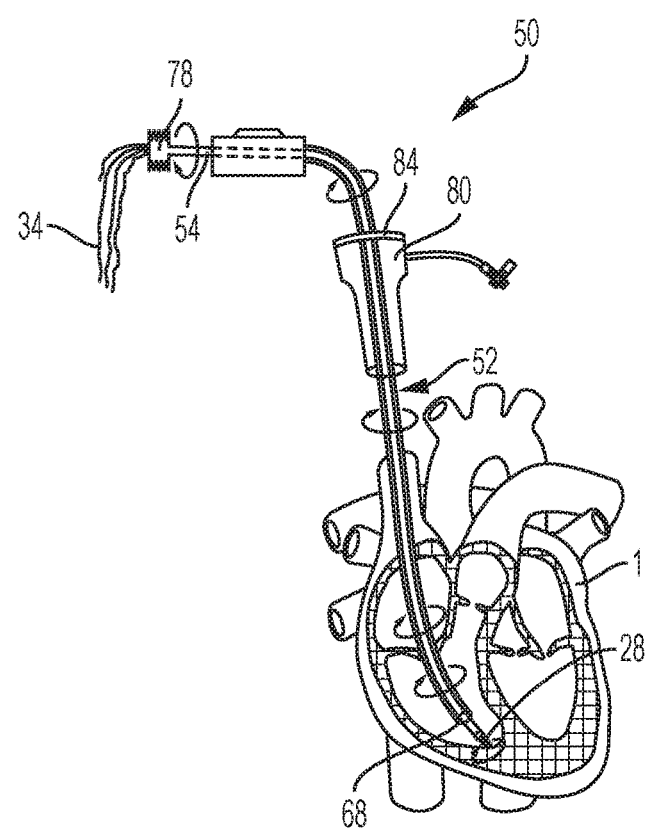
FIG. 4B is a perspective view of the anchor delivery system of FIG. 3, in which the anchor delivery system is delivering a portion of the tether, connected to the anchor, of FIG. 2 into the right ventricle.

With the anchor screw 28 of the anchor 19, connected to tether 18 via anchor cap 30, positioned adjacent to the anchoring site 62, the proximal end 66 of the anchor delivery rod 54 is rotated to cause corresponding rotation of the anchor cap 30 as illustrated in FIG. 4B. For example, the rotating handle 78 is rotated in a first direction to cause corresponding rotation of the anchor cap. The anchor screw coupled to the anchor cap 30 also rotates and screws into a portion of the intracardiac wall anchoring site 62 such as the ventricular apex 20 until the distal end 36 of the anchor cap is adjacent to the intracardiac wall and/or the tether is securely attached thereto the wall. Note that in this position, the anchor screw 28 does not extend completely through any portion of the heart wall, and trans-apical access is not necessary. Upon placement of the anchor cap 30 in the desired position, the anchor delivery rod 54 and the anchor delivery guide 52 of the anchor delivery system 50 are retracted from the heart 1 as illustrated in FIG. 5A. As such, in FIG. 5B, the cords 32 of tether 18, coupled to the anchor cap 30, are secured by the anchor screw 28 of anchor 19, and remain within the right ventricle and the valve delivery system 100 is employed.

As shown in FIG. 5B, after placement of the anchor cap 30 of anchor 19, the at least one cord 32 of the tether 18 extends from the anchor cap through the tricuspid annulus and into the right atrium 2. A suture 34 is coupled to the proximal end of each cord and extends through the superior (or inferior) vena cava and out of the heart 1.

If more than one tether 18, connected to an anchor 19, is delivered, each anchor 19 is secured by its anchor screw 28, and this process is repeated until all tethers, connected to anchors, have been securely attached to the heart wall. In one aspect and as illustrated in FIGS. 6A and 6B, the assembly 10 utilizes two anchors and tethers, three anchors and tethers, four anchors and tethers, or more anchors and tethers are also contemplated.

With the anchor screw 28 secured to the ventricular apex and the tether 18 in place, the valve delivery assembly 100 may now be utilized to introduce and position the valve 12.

The Valve Delivery System

Referring now to FIGS. 7A and 7B, the valve delivery assembly 100 for positioning and deploying the valve 12 at the desired deployment site 13 is illustrated. As shown, the valve delivery assembly 100 comprises a valve delivery guide 102, a nosecone 104, a valve deployment knob 106 and at least one atrial positioning rod 108. In this aspect, the valve delivery guide has a distal end 110, an opposed proximal end 112 and an inner guide lumen 114 extending therebetween, the inner guide lumen sized and configured so that the valve 12 and other system components is extended therethrough. In another aspect, at least a portion of the valve delivery guide 102 is flexible so that a tip 116 at the distal end of the valve delivery guide is positioned past the deployment site 13 and into the right ventricle 3.

The valve deployment knob 106 is coupled to the proximal end 112 of the valve delivery guide 102. A central channel 118 is defined by the valve deployment knob 106 and is in fluid communication with the inner guide lumen 114 so that the atrial positioning rod 108, the J-wire 82 and/or the at least one suture 34 extend through the central channel 118 and into the inner guide lumen 114. In another aspect, the valve deployment knob 106 is rotatable and configured such that rotation of the knob 106 in a first direction causes the sheath 102 around the valve 12 to be removed. The nosecone 104 may be a conventional nosecone coupled to the valve delivery guide 102 and configured to guide the valve 12 to the deployment site 13.

Figure 8B:
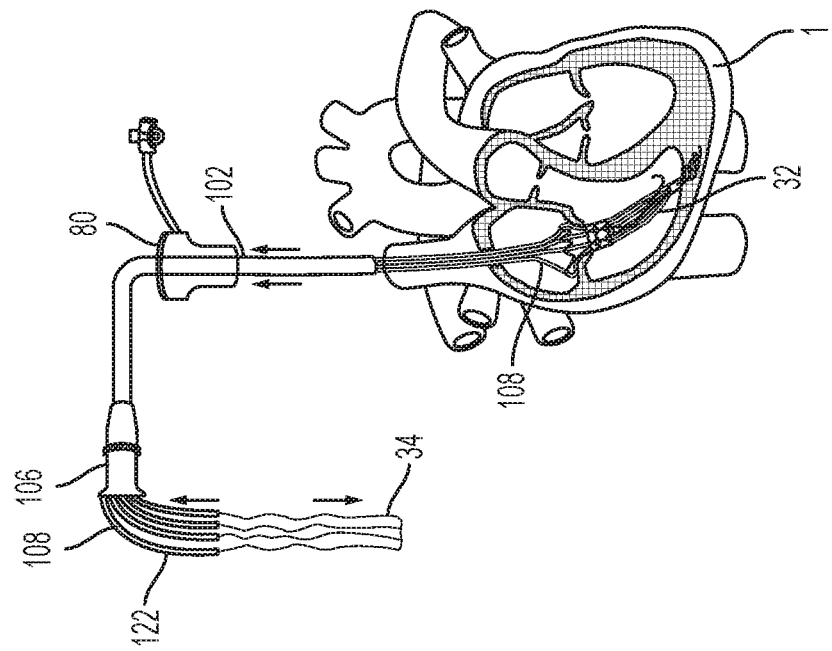
FIG. 8B is a perspective view of a valve of the transcatheter valve system of FIG. 1, in which the valve has been positioned in the tricuspid annulus by the valve delivery system of FIG. 7A.
Figure 8A:
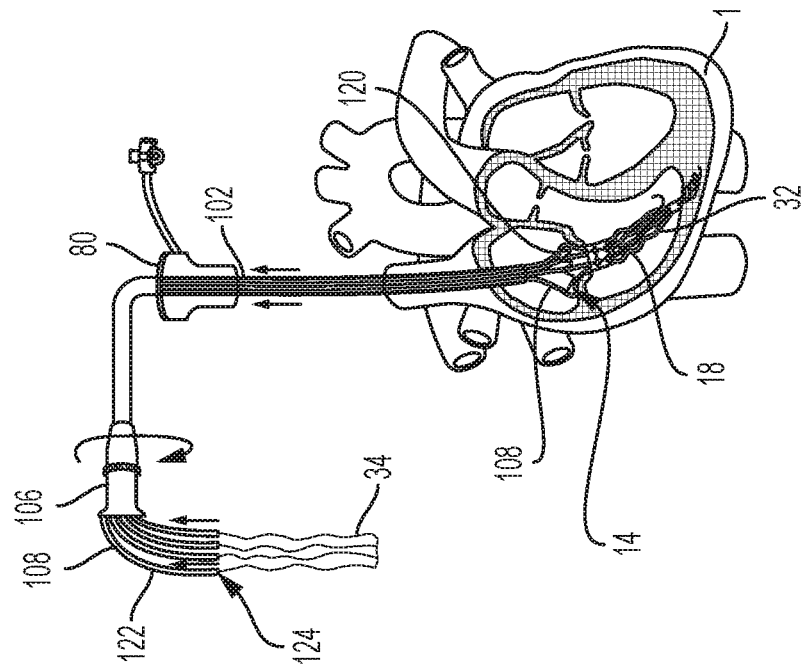
FIG. 8A is a perspective view of a valve of the transcatheter valve system of FIG. 1, in which the valve is being positioned in the tricuspid annulus by the valve delivery system of FIG. 7A.
Figure 12A:
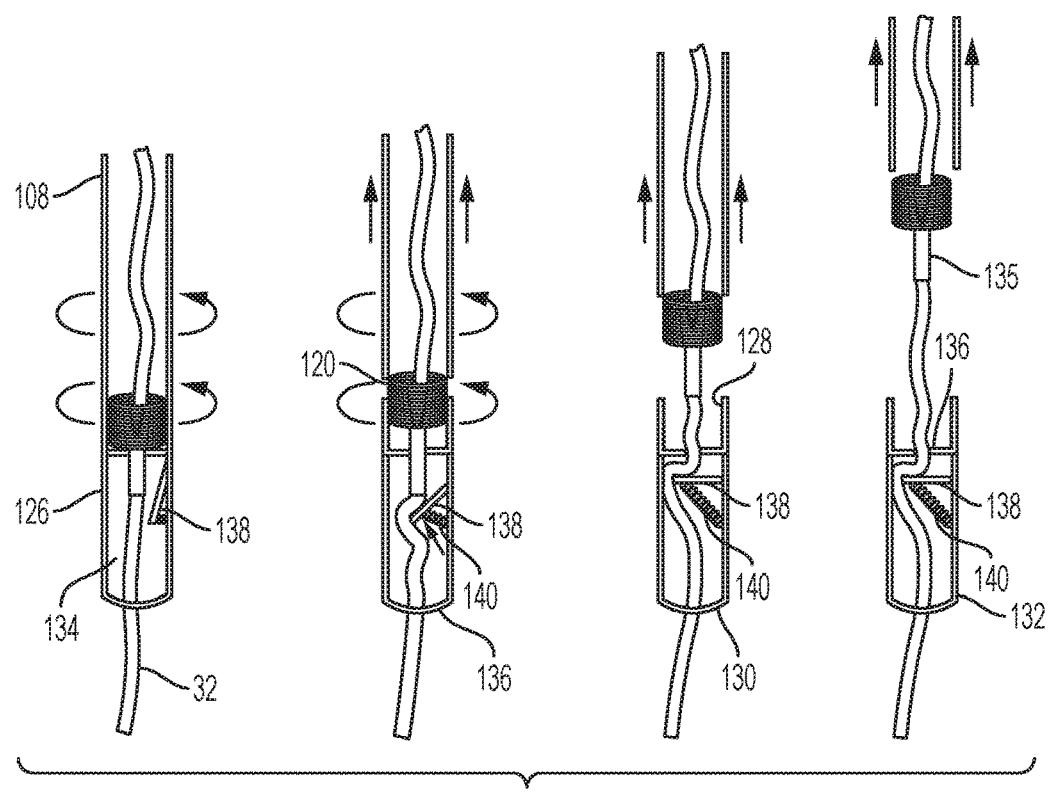
FIG. 12A is an elevational view of an atrial lock of the transcatheter valve system of FIG. 1, according to one aspect.
Figure 12B:
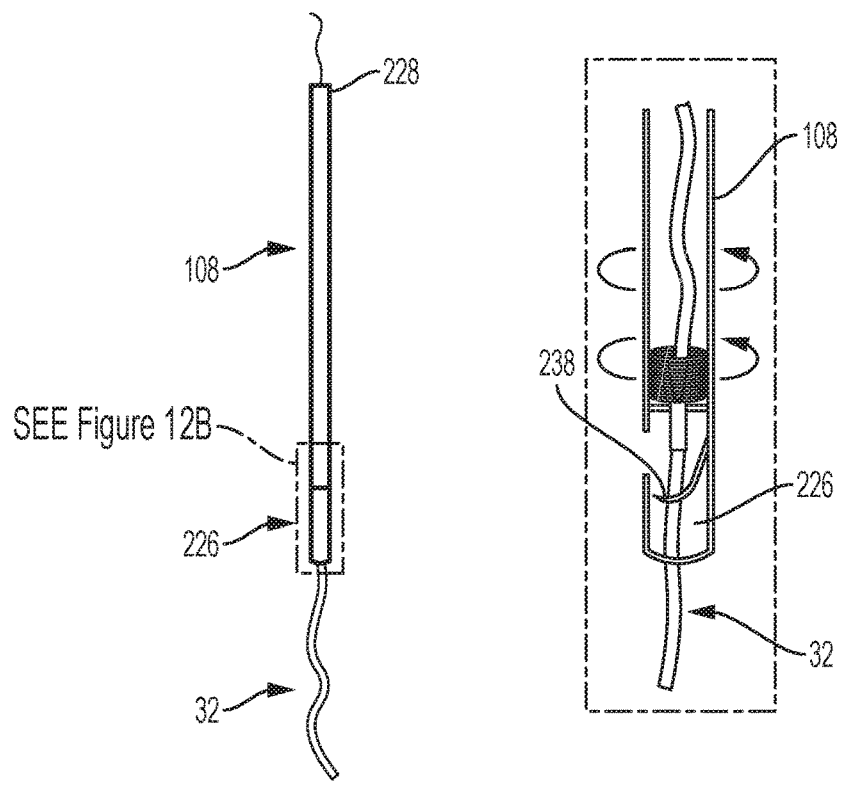
FIG. 12B is a magnified elevational view of the atrial lock of FIG. 12A.

With reference to FIGS. 8A and 8B, the at least one atrial positioning rod 108 has a distal end 120, an opposed proximal end 122 and an inner rod lumen 124 extending there between, the inner rod lumen being sized and configured so that a portion of a suture 34 and/or a cord 32 is inserted therethrough. In another aspect, at least a portion of the atrial positioning rod 108 is flexible so that the distal end 120 of the atrial positioning rod is positioned at or adjacent to the deployment site 13.

The Atrial Skirt Lock

The at least one atrial positioning rod 108 comprises a detachable lock 126 positioned on or adjacent the distal end 120 of the rod, as illustrated in FIGS. 9-14. In one aspect, the detachable lock is configured to securely attach the at least one cord 32 to a portion of the right atrium 2. Thus, the distal end 40 of the cord is securely attached to the anchor cap 30 in the right ventricle 3, and the detachable lock 126 securely attaches the cord 32 in the right atrium.

FIGS. 10A, 10B and 11A-11D illustrate one embodiment of the detachable lock 126. In one aspect, the lock has a first end 128, an opposed second end 130 and a sidewall 132 that cooperate to define a central cavity 134. In another aspect, the first end is threaded and configured to matingly engage complementary threads on the distal end 120 of the atrial positioning rod 108. An opening 136 is defined in each of the first and second ends of the lock 126 so that a portion of the cord 32 extends through both openings and through the central cavity. In use, described more fully below, the detachable lock is selectively attached to the atrial positioning rod by rotating the rod 108 in a first direction, and the detachable lock 126 is selectively detached from the atrial positioning rod by rotating the rod 108 in a second direction that is opposed to the first direction.

In one aspect, the detachable lock 126 further comprises a clamp 138 movable about and between a first locked position, in which a portion of the clamp secures the cord 32 in the desired position, and a second unlocked position, in which the clamp does not secure the cord in the desired position. A biasing member 140 such as a spring and the like is configured to urge the clamp 138 to the first locked position. A tab 135 or other protrusion extending away from the distal end 120 of the atrial positioning rod 108 is configured to maintain the clamp in the second, unlocked position when the detachable lock is attached to the rod 108.

FIGS. 12A-14D illustrate another embodiment of a detachable lock 226. In one aspect, the lock has a first end 228, an opposed second end 230 and a sidewall 232 that cooperate to define a central cavity 234. In another aspect, the first end is threaded and configured to matingly engage complementary threads on the distal end 120 of the atrial positioning rod 108. An opening 236 is defined in each of the first and second ends of the lock 226 so that a portion of the cord 32 extends through both openings and through the central cavity. In use, described more fully below, the detachable lock is selectively attached to the atrial positioning rod by rotating the rod 108 in a first direction, and the detachable lock 226 is selectively detached from the atrial positioning rod by rotating the rod 108 in a second direction that is opposed to the first direction.

In one aspect, the detachable lock 226 further comprises an atrial anchor 238 movable about and between a first locked position, in which a portion of the atrial anchor secures the cord 32 in the desired position, and a second unlocked position, in which the atrial anchor does not secure the cord in the desired position. A biasing member 240 such as a spring and the like is configured to urge the atrial anchor 238 to the first locked position. A tab 135 or other protrusion extending away from the distal end 120 of the atrial positioning rod 108 is configured to maintain the atrial anchor in the second, unlocked position when the detachable lock is attached to the rod 108.

In one aspect, an anchor exit port 242 is defined in a portion of the sidewall 232 of the detachable lock 226. In this aspect, the anchor exit port is sized and shaped so that, in the first locked position, a hook 244 or other grasping element positioned on a tip of 246 of the atrial anchor extends through the port 242 and outside of the central cavity 234. In use, in the first locked position, the hook securely anchors the detachable lock (and thus, the cord 32) to a portion of the atrium 2. With reference now to FIG. 15, the assembly 10 further comprises a suture cutter 148 sized and configured to pass over the at least one suture 34 through the valve delivery sheath 80 to cut the at least one suture 34.

In use, the assembly 10 implants the valve 12 with a transcatheter approach by placing a right ventricular anchor first. The valve position would not require pulling a tether 18 through an intracardiac wall such as the ventricular apex 20 of the heart 1, because the valve 12 moves freely over the tether until the desired valve position is achieved. After the desired valve position is achieved, the at least one atrial positioning rod 108 urges the atrial sealing skirt 14 into position and is locked into place via a detachable lock 126, 226 at the end of each positioning rod. The valve is repositioned or retrieved until release of the sutures 34 that extend through each atrial positioning rod 108.

Figure 14E:
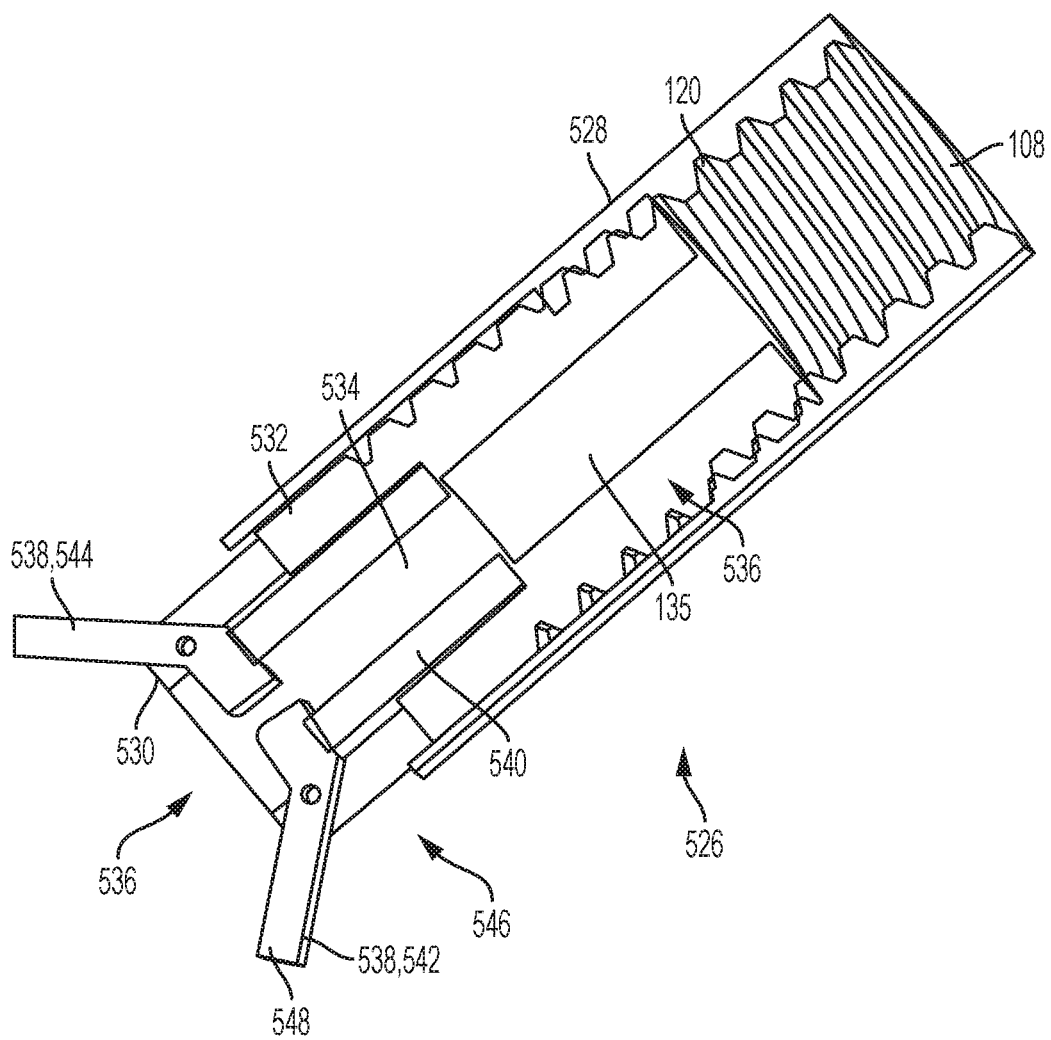
FIG. 14E is a perspective view of an atrial lock of the transcatheter valve system of FIG. 1, according to one aspect.

FIG. 14E illustrates another embodiment of a detachable lock 526. In one aspect, the lock has a first end 528, an opposed second end 530 and a sidewall 532 that cooperate to define a central cavity 534. In another aspect, the first end is threaded and configured to matingly engage complementary threads on the distal end 120 of the atrial positioning rod 108. An opening 536 is defined in each of the first and second ends of the lock 526 so that a portion of the cord 32 extends through both openings and through the central cavity. In use, described more fully below, the detachable lock is selectively attached to the atrial positioning rod by rotating the rod 108 in a first direction, and the detachable lock 526 is selectively detached from the atrial positioning rod by rotating the rod 108 in a second direction that is opposed to the first direction.

In one aspect, the detachable lock 526 further comprises at least one atrial anchor 538 movable about and between a first locked position, in which a portion of the atrial anchor secures the cord 32 in the desired position, and a second unlocked position, in which the atrial anchor does not secure the cord in the desired position. Optionally, the atrial anchor comprises a first atrial anchor 542 and a second atrial anchor 544. In another aspect, the atrial anchor comprises a cam lever arm. A biasing member 540 such as a spring and the like is configured to urge the atrial anchor 538 to the first locked position. In a further aspect, the biasing member is a compressible polymer. A tab 135 or other protrusion extending away from the distal end 120 of the atrial positioning rod 108 is configured to maintain the atrial anchor in the second, unlocked position when the detachable lock is attached to the rod 108.

In one aspect, an anchor exit port 546 is defined in a portion of the sidewall 532 of the detachable lock 526. In this aspect, the anchor exit port is sized and shaped so that, in the first locked position, a portion 548 of the atrial anchor 538 extends through the port 546 and outside of the central cavity 534. In use, in the first locked position, the atrial anchor securely anchors the detachable lock (and thus, the cord 32) to a portion of the atrium 2.

With reference now to FIG. 15, the assembly 10 optionally further comprises a suture cutter 148 sized and configured to pass through the valve delivery sheath 80 to cut the at least one suture 34.

The Valve Delivery and Positioning Method

In use, the assembly 10 implants the valve 12 with a transcatheter approach by placing a right ventricular anchor first. The valve position would not require pulling a tether 18 through an intracardiac wall such as the ventricular apex 20 of the heart 1, because the valve 12 moves freely over the tether until the desired valve position is achieved. After the desired valve position is achieved, the at least one atrial positioning rod 108 urges the atrial sealing skirt 14 into position and is locked into place via a detachable lock 126, 226 at the end of each positioning rod. The valve is repositioned or retrieved until release of the sutures 34 that extend through each atrial positioning rod 108.

Referring now to FIG. 7A, the valve delivery assembly 100 can then be inserted over the J-wire 82 and into a portion of the heart 1. Before the valve delivery guide 102 is inserted into sheath 80 en route to the heart, the valve 12 is preloaded into the distal end 110 of the valve delivery guide 102. At least a portion of the suture 34 is threaded through the at least one bore 15 defined in the outer wall 17 of the valve 12, illustrated in FIGS. 7B and 7C, tracking into the inner guide lumen 114 of the valve delivery guide 102. As the valve 12, inside distal end 110, and the valve delivery guide 102 move as a unit over J-wire 82, a portion of the at least one cord can extend through and away from the distal end 110 of the valve delivery guide, and a portion of the at least one suture can extend through and away from the proximal end 112 of the valve delivery guide 102. The valve delivery guide is positioned so that the tip 116 at the distal end of the valve delivery guide 102 is passed through the deployment site 13 and into the right ventricle 3.

The valve 12, which has been preloaded into the distal end 110 of the valve delivery guide 102, is positioned at deployment site 13. In one aspect, and prior to insertion into the valve delivery guide, each suture 34 is threaded through the at least one bore 15 defined in the outer wall 17 of the valve 12, illustrated in FIGS. 7B and 7C. In another aspect, similar bores (not shown) is defined in the atrial sealing skirt 14 so that each suture is threaded through the bore defined in the sealing skirt. As the valve 12 and valve delivery guide 102 are moved as a unit toward the deployment site, the valve 12 will reach the end of the suture and a portion of the cord 32 will become threaded through the bore 15 defined in the valve. In one aspect, the valve 12 and valve delivery guide 102 can slide up and down the at least one cord until the desired deployment site 13 has been reached. That is, the valve is free floating on the cord 32 until locked in placed by the detachable lock 126, 226.

As is appreciated, with the valve 12 in the desired deployment site 13, the valve deployment knob 106 retracts the distal end 110 of the valve delivery guide 102 while the valve 12 remains fixed in position, thereby "unsheathing" the valve 12 so that the valve and/or the atrial sealing skirt 14 will expand to its full, uncompressed size. Optionally, in one aspect, because the valve position is adjusted, the valve deployment knob 106 is used to retract the distal end 110 of the valve delivery guide 102, thereby "unsheathing" the valve 12 so that the valve and/or skirt will expand to its full, uncompressed size with the valve near the desired deployment site.

An atrial positioning rod 108 is then be inserted over each suture 34 such that a portion of each suture is in the inner rod lumen 124 and a portion of each suture extends from the proximal end 122 of the positioning rod. With reference to FIGS. 8A and 8B, the positioning rod 108 is inserted through the valve delivery guide 102 until a portion of the cord 32 is in the inner rod lumen and the distal end 120 of the positioning rod (with the detachable lock 126, 226 attached thereto) is adjacent to the atrial sealing skirt 14. The positioning rods 108 are pushed down by the user until the sealing skirt is in a desired position relative to the tricuspid annulus. With the sealing skirt 14 and the valve 12 in a desired position at the deployment site 13, each suture 34 is pulled taut by the user, which will in turn pull slack through the inner rod lumen 124 until each cord 32 is taut. For example, the end of a suture that extends from the proximal end 122 of the atrial positioning rod is pulled by a user to adjust tension in the corresponding cord. In one aspect, differential tension is applied to the cord 32 by adjusting the force applied to the suture 34. For example, if the user pulls a first suture harder than a second suture 34, the tension in the cord 32 corresponding to the first suture is higher than the tension in the cord coupled to the second suture 34.

Referring now to FIGS. 9A and 9B, each atrial positioning rod 108 is then rotated in a first direction to lock each detachable lock 126, 226 against the atrial sealing skirt 14 and to the cord 32. Thus, the valve 12 is locked by the detachable lock on the atrial side of the tricuspid annulus. Continued rotation in the first direction detaches the lock 126, 226 from the positioning rod. When the lock has been detached from the positioning rod 108, the rod is retracted from the heart 1 through the valve delivery guide 102. With the positioning rods 108 retracted, the cord 32 of the at least one tether 18 couples the valve to the intracardiac anchor wall such as the ventricular apex 20. The detachable lock 126, 226 in the locked position prevents the proximal end 42 of the cord from moving relative to the sealing skirt 14, thereby securely fixing the valve 12 in place in the deployment site 13.

As illustrated in FIGS. 15A and 15B, with the valve 12 securely fixed in the deployment site 13, the suture cutter 148 is advanced over the sutures 34 and to the detachable lock 126, 226. The suture cutter then cuts the distal end of each suture just above the detachable lock. The sutures and the suture cutter are then removed from the heart 1.

In one aspect, prior to cutting of the sutures 34, the valve 12 is retrieved or repositioned. For example, if it is determined that the valve is to be removed or repositioned, an atrial positioning rod 108 is positioned over each suture so that a portion of the suture is in the inner rod lumen 124. When the distal end 120 of the positioning rod is adjacent to or in contract with the detachable lock 126, 226, rotation of the positioning rod 108 in a second direction that is opposed to the first direction attaches the detachable lock to the distal end of the positioning rod. Continued rotation in the second direction unlocks the lock from the cord 32. With each cord unlocked, the valve is removed from and/or repositioned in the deployment site 13.

In another aspect, the valve 12 could be repositioned and/or removed days to weeks after valve deployment. In this aspect, the sutures are not cut, but wrapped around a spool or other wrapping device. This device could then be attached to the atrial skirt 14 of the valve 12. Days after deployment of the valve and completion of the procedure, the spool/wrapping device could be re-captured, allowing un-wrapping and retrieval of the sutures. An atrial positioning rod 108 could be positioned over each suture so that a portion of the suture is in the inner rod lumen 124. When the distal end 120 of the positioning rod is adjacent to or in contract with the detachable lock 126, 226, rotation of the positioning rod 108 in the second direction that is opposed to the first direction attaches the detachable lock to the distal end of the positioning rod. Continued rotation in the second direction unlocks the lock from the cord 32. With each cord unlocked, the valve is removed from and/or repositioned in the deployment site 13.

The Epicardial Tether System

Figure 16:
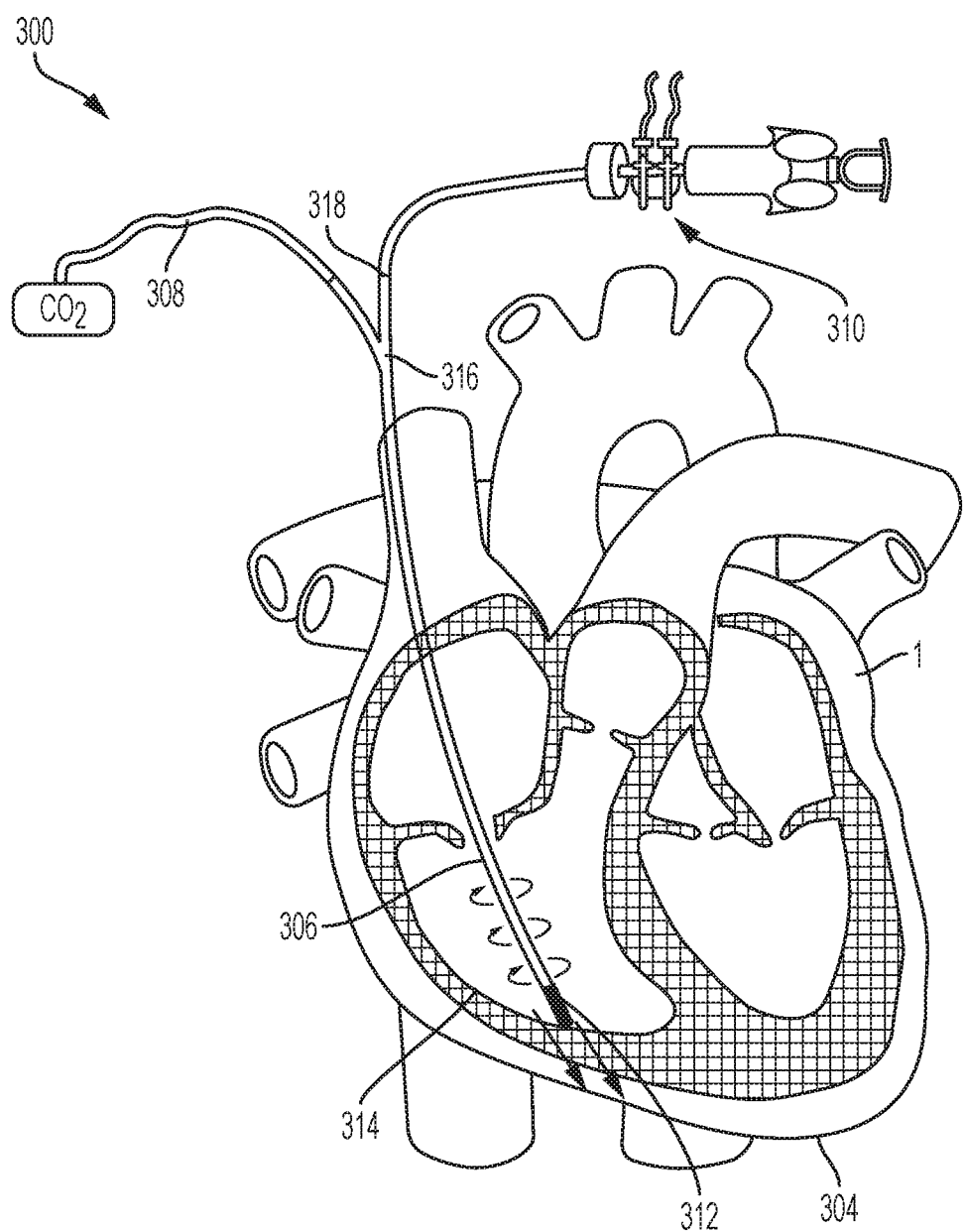
FIG. 16 is a perspective view of an epicardial tether system for positioning an anchor in the pericardial space, according to one aspect.

In one embodiment, illustrated in FIGS. 16-23, the assembly 10 comprises an epicardial tether system 300 for positioning an anchor 302 in the pericardial space 304. In one aspect, the epicardial tether comprises a catheter 306, a $CO_2$ gas line 308 and a manifold 310. In another aspect, the catheter is a micro-catheter having a distal end 312 configured to be screwed and/or otherwise urged through at least a portion of the wall of the heart 1. For example, and as illustrated in FIG. 16, the distal end of the micro-catheter engages the endocardium 314 of the heart. The micro-catheter 306 also has a proximal end 316 opposed to the distal end and an inner catheter lumen 318. The proximal end of the micro-catheter is coupled to the $CO_2$ gas line 308 and the manifold 310 so that the $CO_2$ gas line and the manifold are in sealed fluid communication with the inner catheter lumen.

Figure 17:
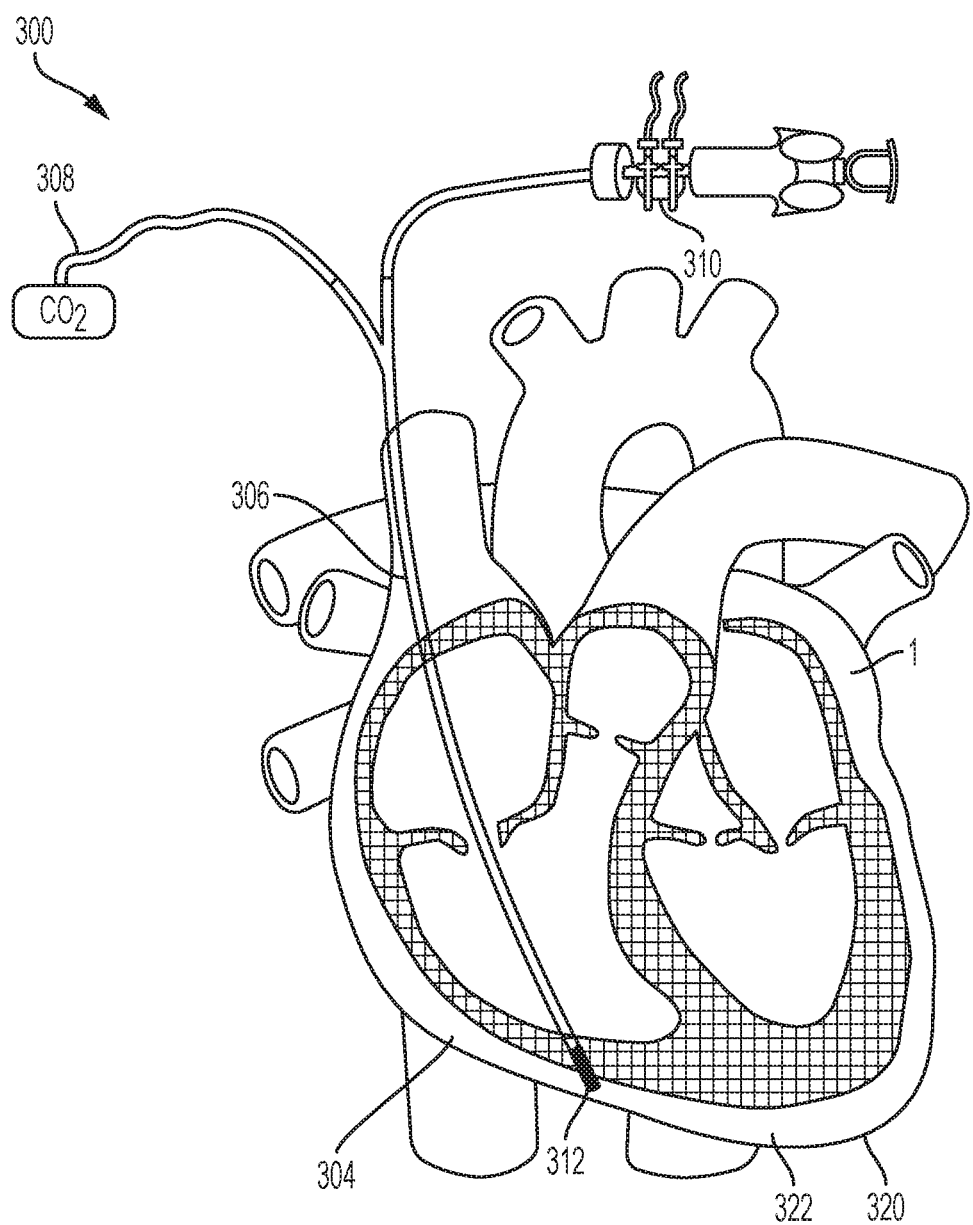
FIG. 17 is a perspective view of the epicardial tether system of FIG. 16, in which a portion of a catheter of the system has entered the pericardial space.

Referring now to FIG. 17, the distal end 312 of the micro-catheter 306 is urged through the heart wall until the distal end of the micro-catheter is positioned in the pericardial space 304 by the pericardium 320. In one aspect, a contrasting agent 322 is injected from the manifold 310 through the inner catheter lumen 318 and into the pericardial space to verify that the distal end 312 of the micro-catheter 306 is in the pericardial space 304.

Figure 18:
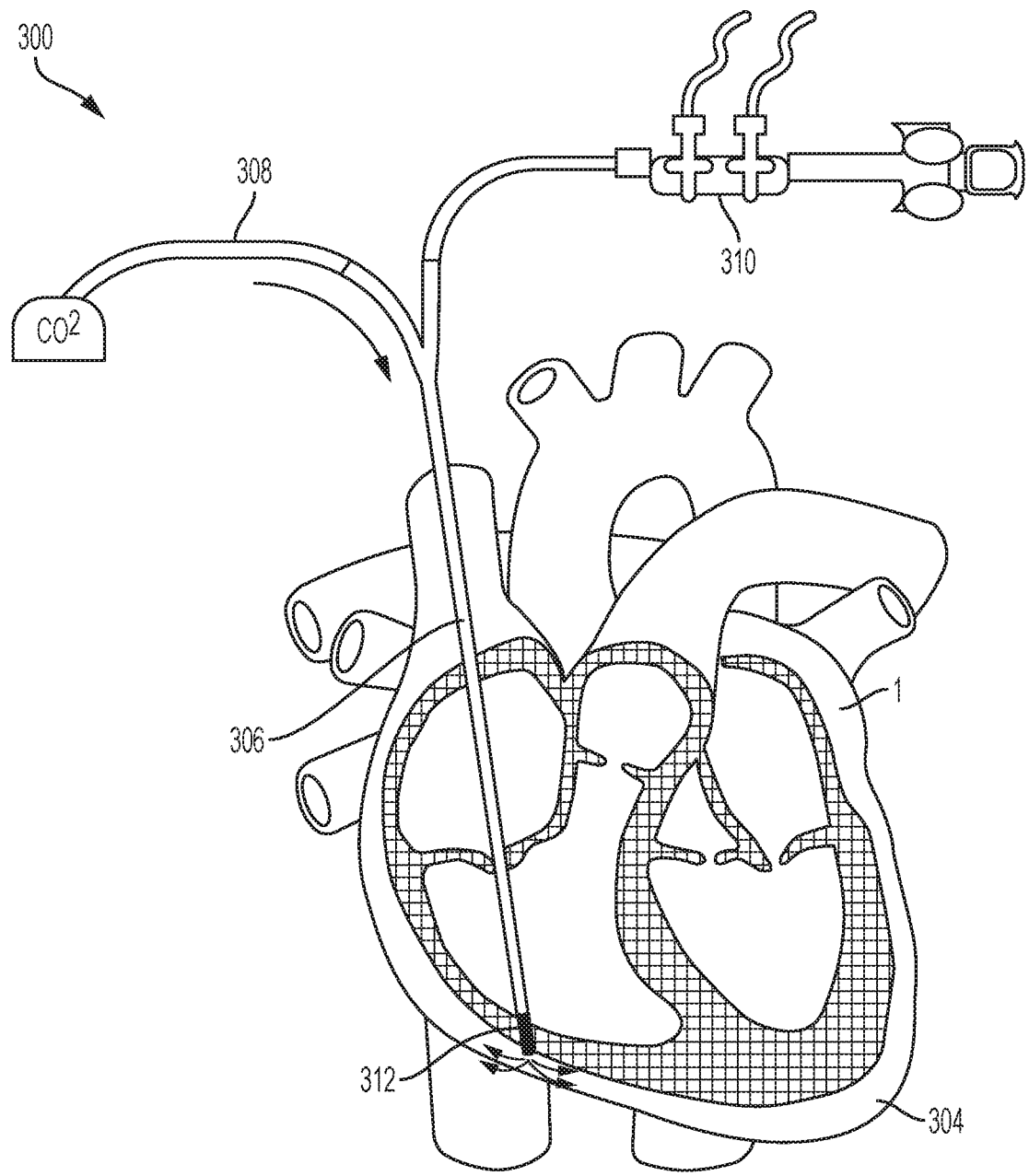
FIG. 18 is a perspective view of the epicardial tether system of FIG. 16, in which the pericardial space has been insufflated.

Once the distal end 312 of the micro-catheter 306 has been positioned in the pericardial space 304, carbon dioxide is injected from the $CO_2$ gas line 308 through the inner catheter lumen 318 and into the pericardial space 304 to insufflate the space, illustrated in FIG. 18.

Figure 19:
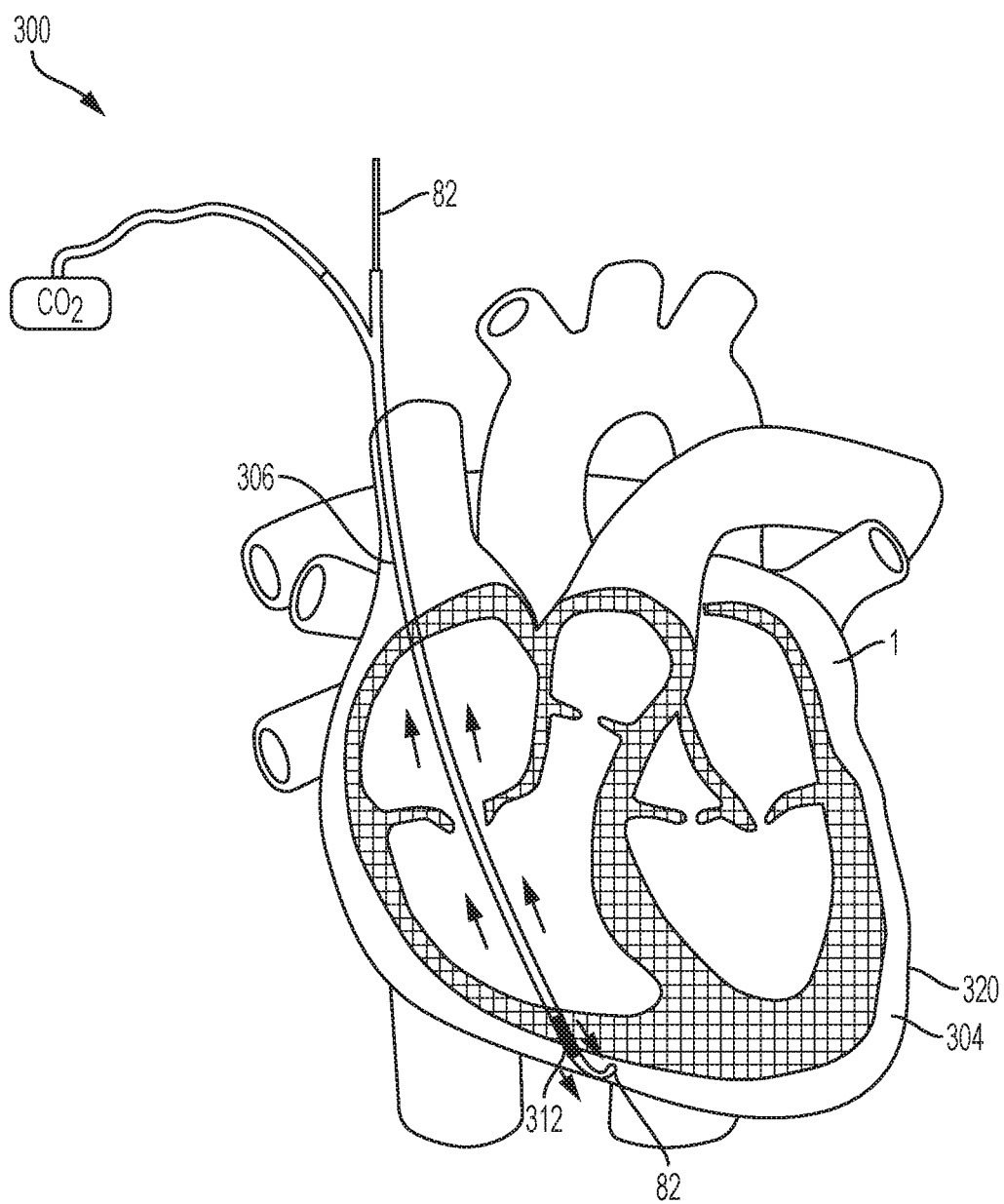
FIG. 19 is a perspective view of the epicardial tether system of FIG. 16, in which a J-wire has been inserted into the insufflated pericardial space.

In one aspect, the J-wire 82 is then advanced through the inner catheter lumen 318 and into the pericardial space 304 as illustrated in FIG. 19. With the J-wire in place, the catheter 306 is removed from the heart 1.

Figure 20:
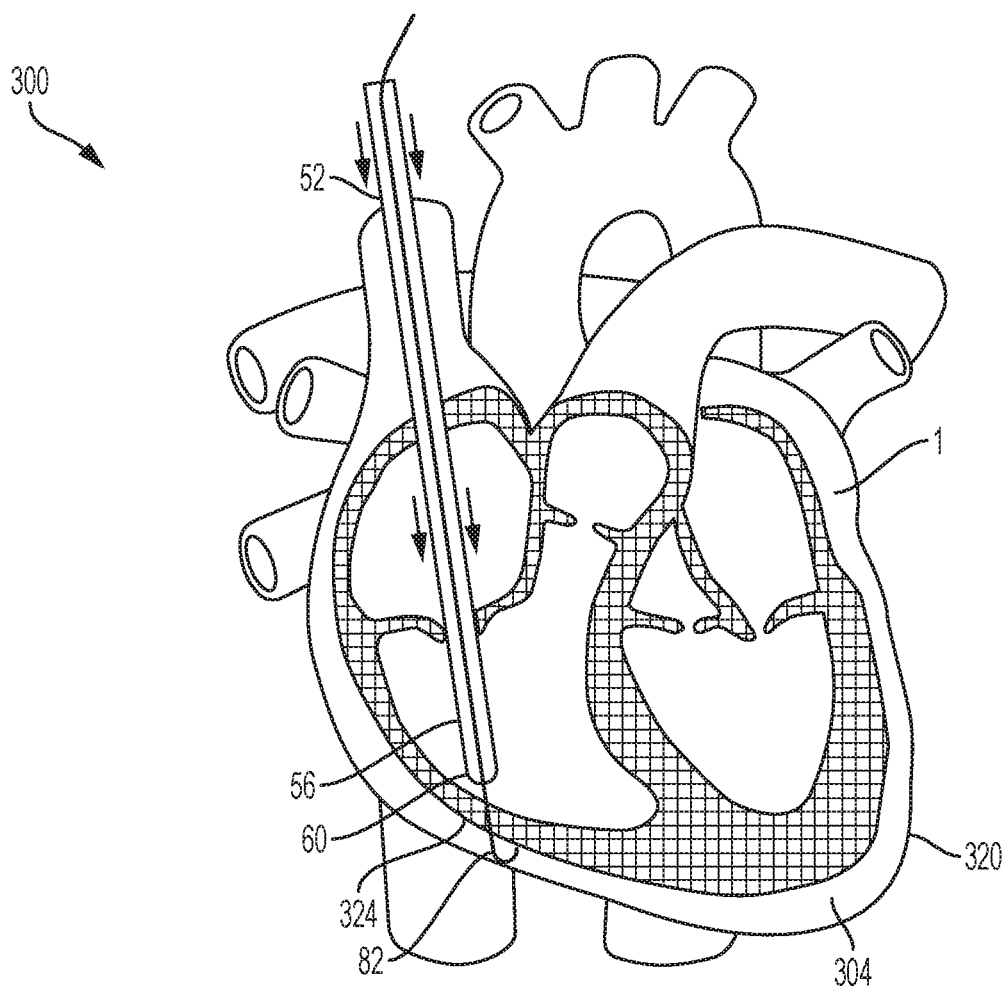
FIG. 20 is a perspective view of the epicardial tether system of FIG. 16, in which an anchor delivery guide of the system approaches the insufflated pericardial space.
Figure 21:
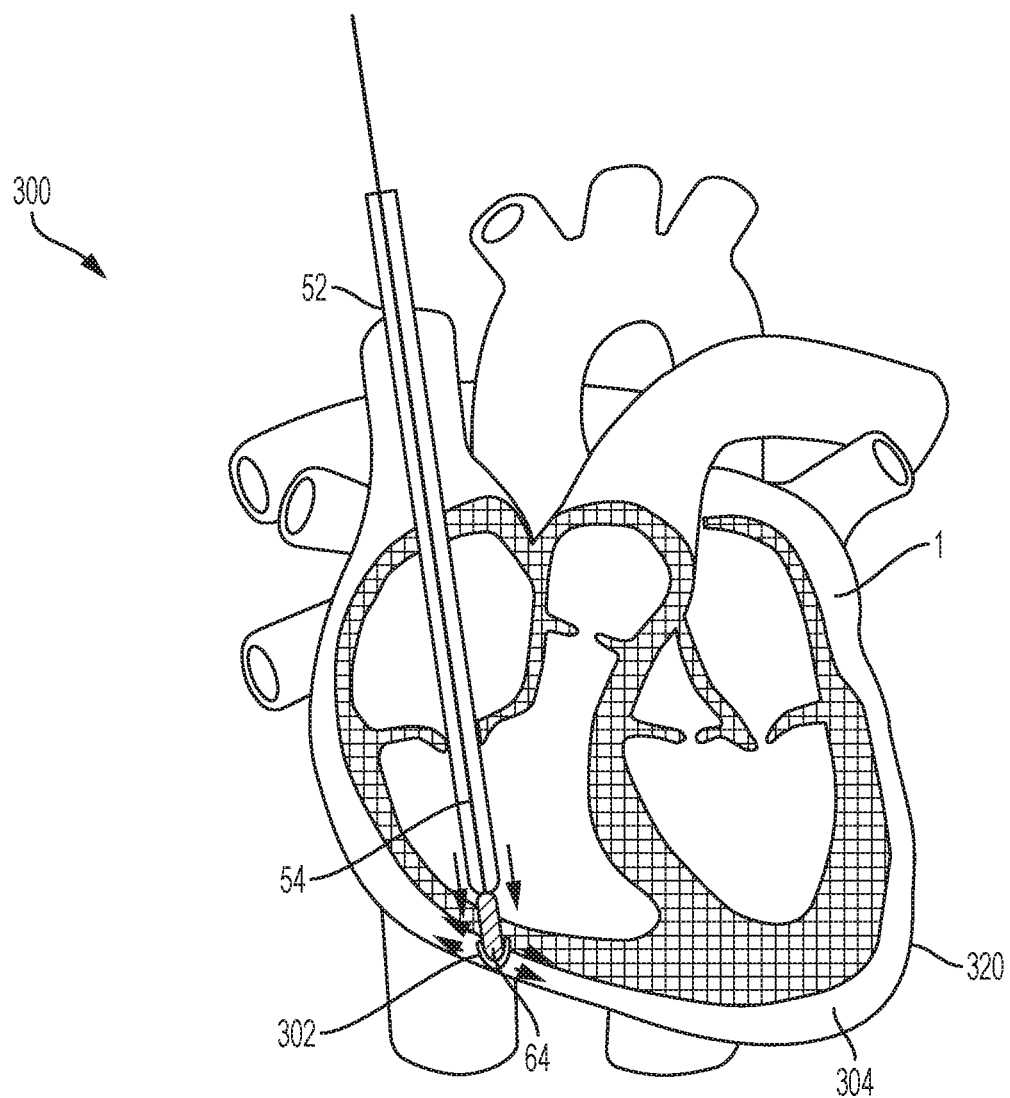
FIG. 21 is a perspective view of the epicardial tether system of FIG. 16, in which an anchor of the system is being positioned in the insufflated pericardial space.

In another aspect, illustrated in FIGS. 20 and 21, the anchor delivery guide 52 is inserted over the J-wire 82 until the tip 60 at the distal end 56 of the anchor delivery guide is positioned at or adjacent an anchoring site 324 in the pericardial space 304. The anchor delivery rod 54 is inserted through the inner guide lumen of the anchor delivery guide 52 until the distal end 64 of the anchor delivery rod is positioned in the pericardial space 304.

Figure 22:
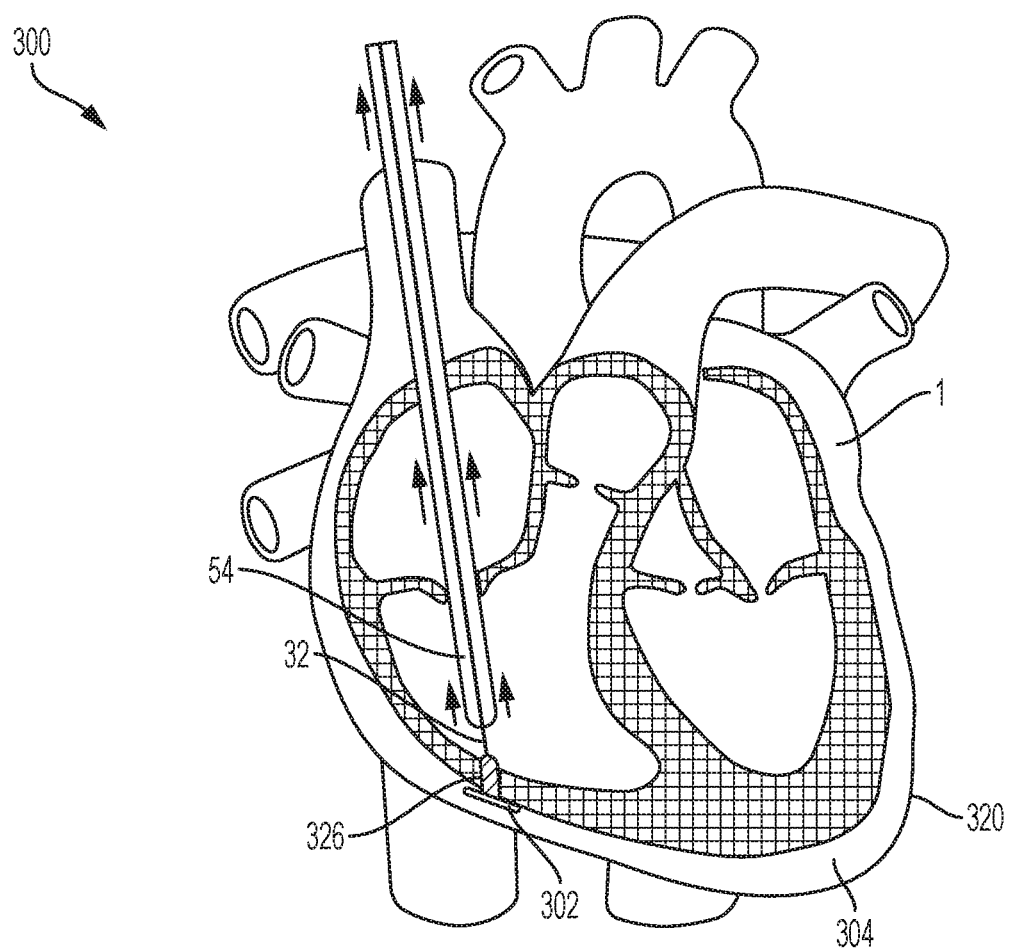
FIG. 22 is a perspective view of the epicardial tether system of FIG. 16, in which an anchor of the system has been deployed in the insufflated pericardial space.

The anchor 302 of the epicardial tether system 300 is coupled to the distal end 64 of the anchor delivery rod 54. In one aspect, the anchor is a self-expanding anchor (that is, the anchor is compressible so that it fits through the inner guide lumen of the anchor delivery guide 52). As illustrated in FIGS. 21 and 22, when the anchor 302 positioned on the distal end of the anchor delivery rod reaches the pericardial space 304, the anchor expands to its full size, thereby locking the anchor 302 in place. A left ventricle portion 326 of the anchor extends through the endocardium and into the left ventricle.

Figure 23:
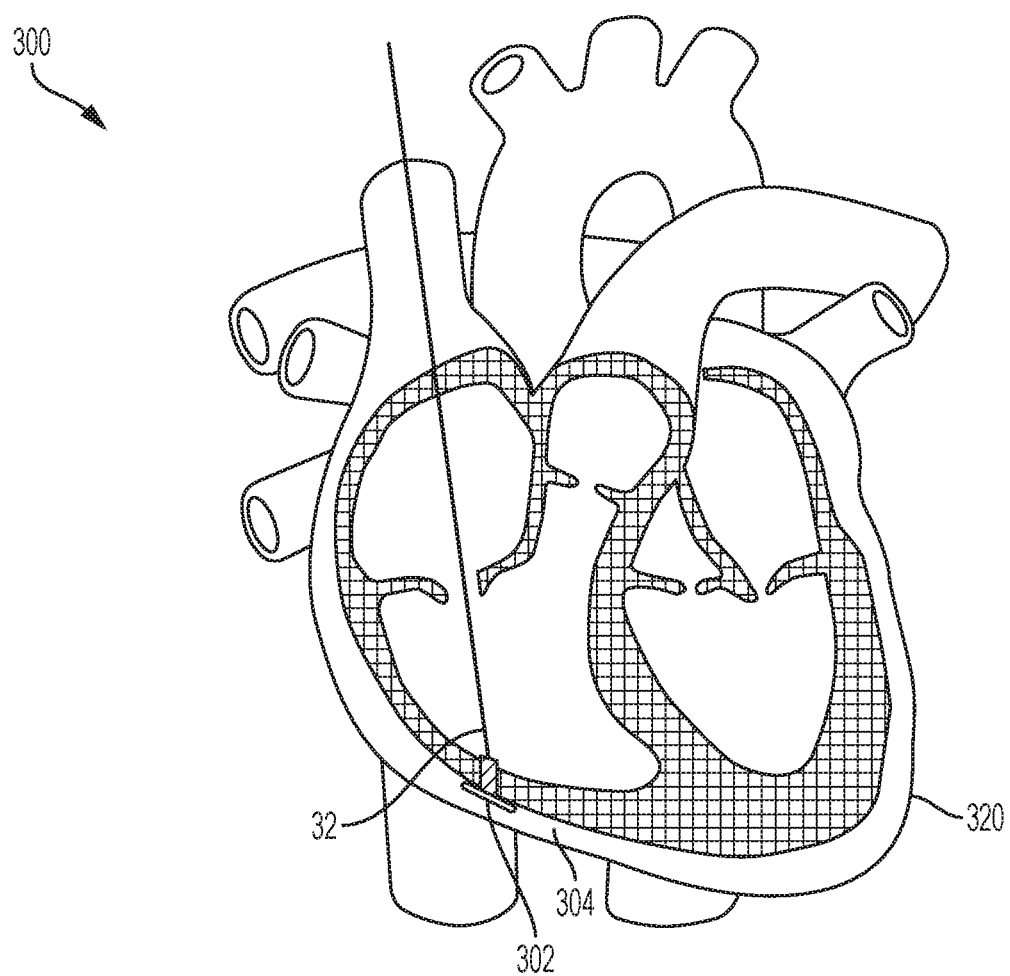
FIG. 23 is a perspective view of the epicardial tether system of FIG. 16, in which an anchor of the system has been deployed in the insufflated pericardial space and delivery devices of the system have been retracted.

In one aspect, the at least one cord 32 is coupled to the anchor 302 prior to deployment in the pericardial space 304. For example, the cord is coupled to the anchor such that the cord is positioned in the inner rod lumen of the anchor delivery rod 54. Thus, when the anchor delivery rod is removed from the heart, as illustrated in FIG. 23, the cord extends from the anchor 302 in the pericardial space through the tricuspid annulus and superior (or inferior) vena cava to outside of the heart. In this aspect, then, the valve 12, detachable locks 126, 226, suture 34 and the like is coupled to the cord 32 as previously described. It is within the scope of the present invention, however, for the anchor to be untethered or uncoupled from the valve upon insertion. As is appreciated, the carbon dioxide in the pericardial space 304 is resorbed and the pericardium returns to its normal position.

The Interventricular Tether System

Figure 24:
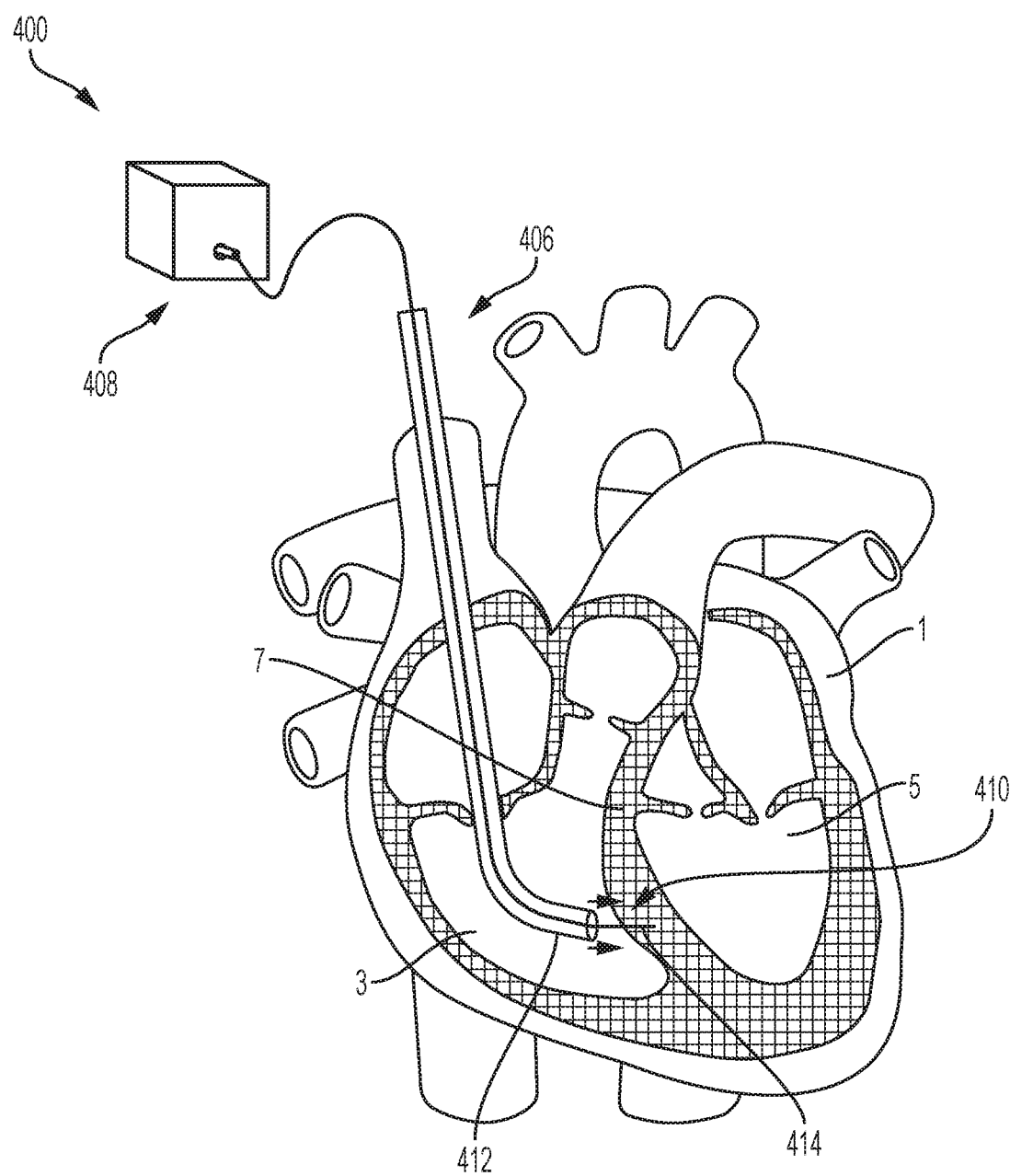
FIG. 24 is a perspective view of an interventricular tether system for positioning an anchor in the left ventricle, according to one aspect.
Figure 25:
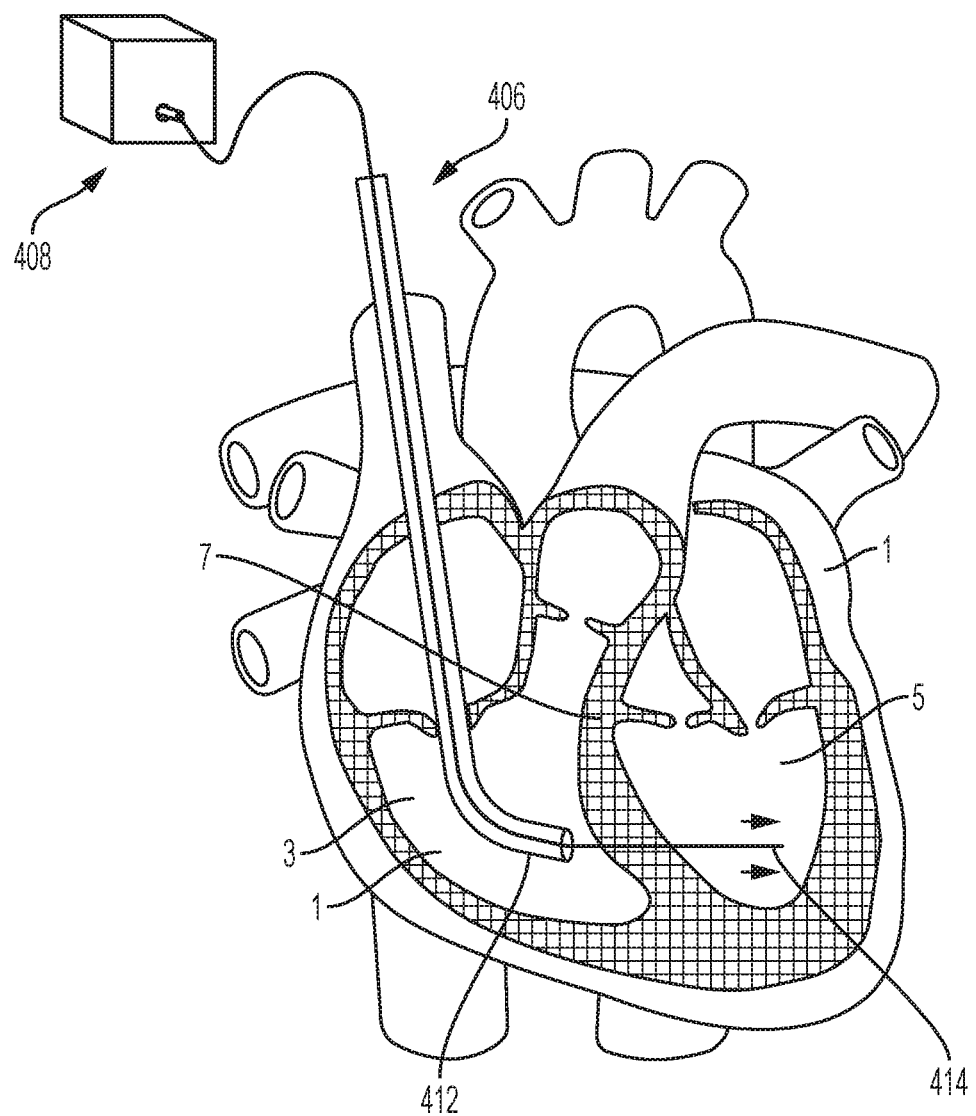
FIG. 25 is a perspective view of the interventricular tether system of FIG. 24, in which an RF wire of the system has crossed the septum and entered the left ventricle.

In another embodiment, illustrated in FIGS. 24-32, the assembly 10 comprises an interventricular tether system 400 for positioning an anchor 402 in the left ventricle 5. In one aspect, the interventricular tether system tether comprises a catheter 406, a radiofrequency ("RF") generator 408 and a RF wire 410 electrically coupled to the RF generator. In another aspect, the catheter is a wire delivery catheter having a distal end 412 configured to be positioned adjacent to or near the septum 7 of the heart 1. In use, RF generated by the RF generator 408 urges a distal end 414 of the RF wire to penetrate the septum, moving from the right ventricle 3 into the left ventricle 5 as shown in FIGS. 24 and 25.

Figure 26:
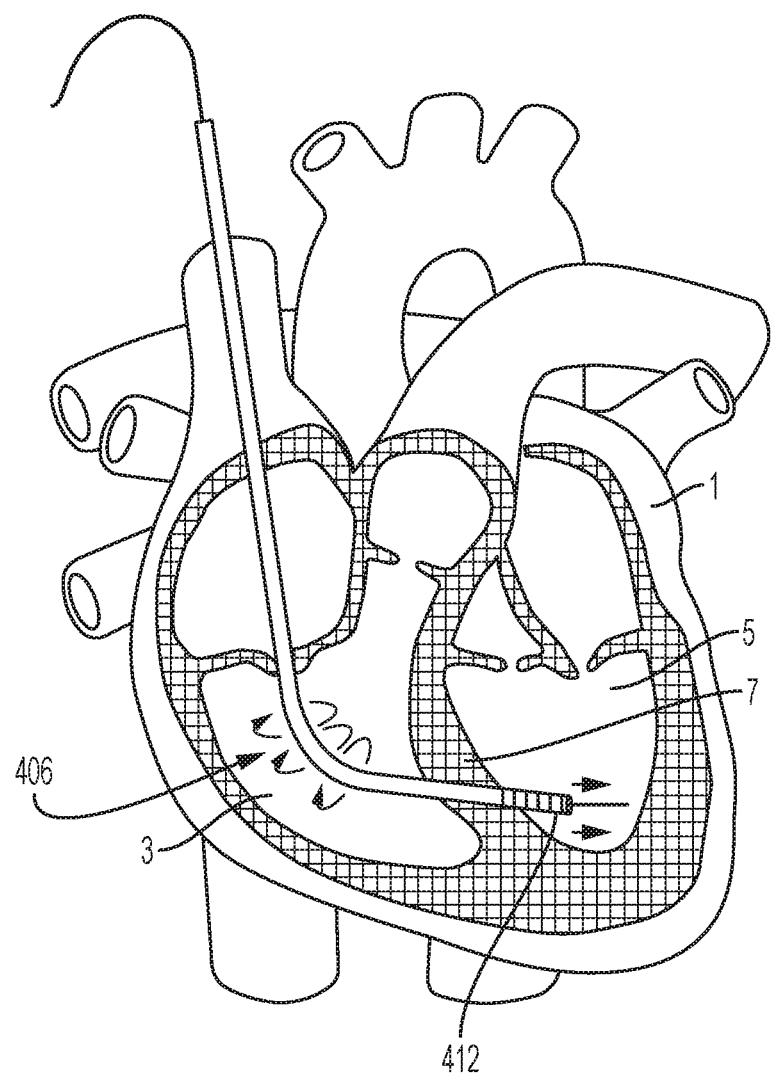
FIG. 26 is a perspective view of the interventricular tether system of FIG. 24, in which a catheter of the system has crossed the septum and entered the left ventricle.
Figure 27:
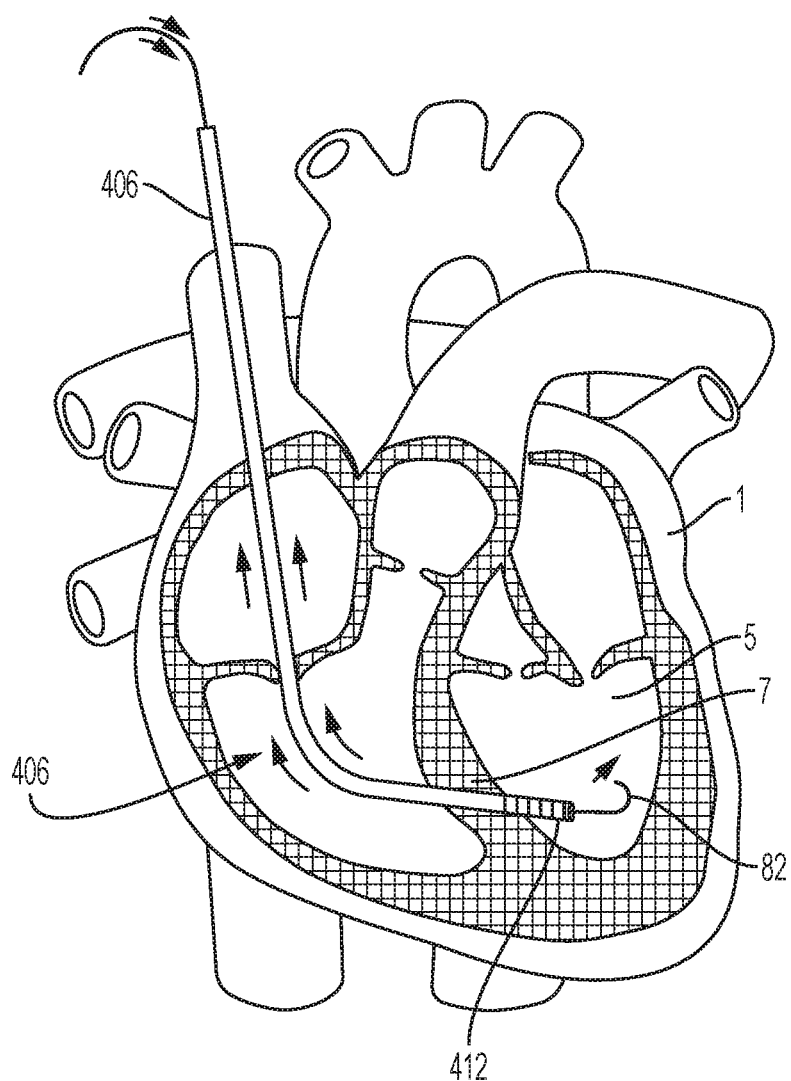
FIG. 27 is a perspective view of the interventricular tether system of FIG. 24, in which a J-wire of the system has been advanced through the catheter and into the left ventricle.

Referring now to FIG. 26, the catheter 406 is then urged into the left ventricle 5. For example, if a portion of the distal end 412 of the catheter is threaded, rotation of the catheter 406 urges the distal end across the septum 7 and into the left ventricle. With a portion of the catheter in the left ventricle, the RF wire is retracted and the J-wire 82 is inserted through the catheter 406 until a portion of the J-wire is in the left ventricle 5, illustrated in FIG. 27.

Figure 28:
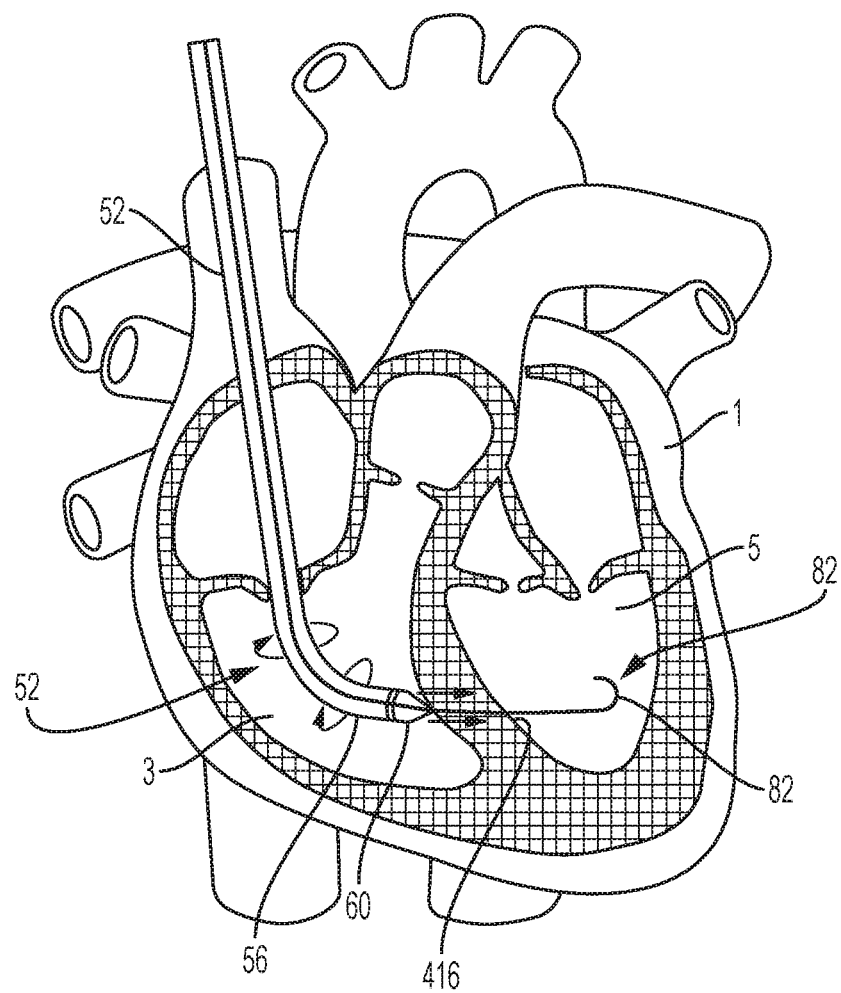
FIG. 28 is a perspective view of the interventricular tether system of FIG. 24, in which a delivery guide of the system approaches the left ventricle.
Figure 29:
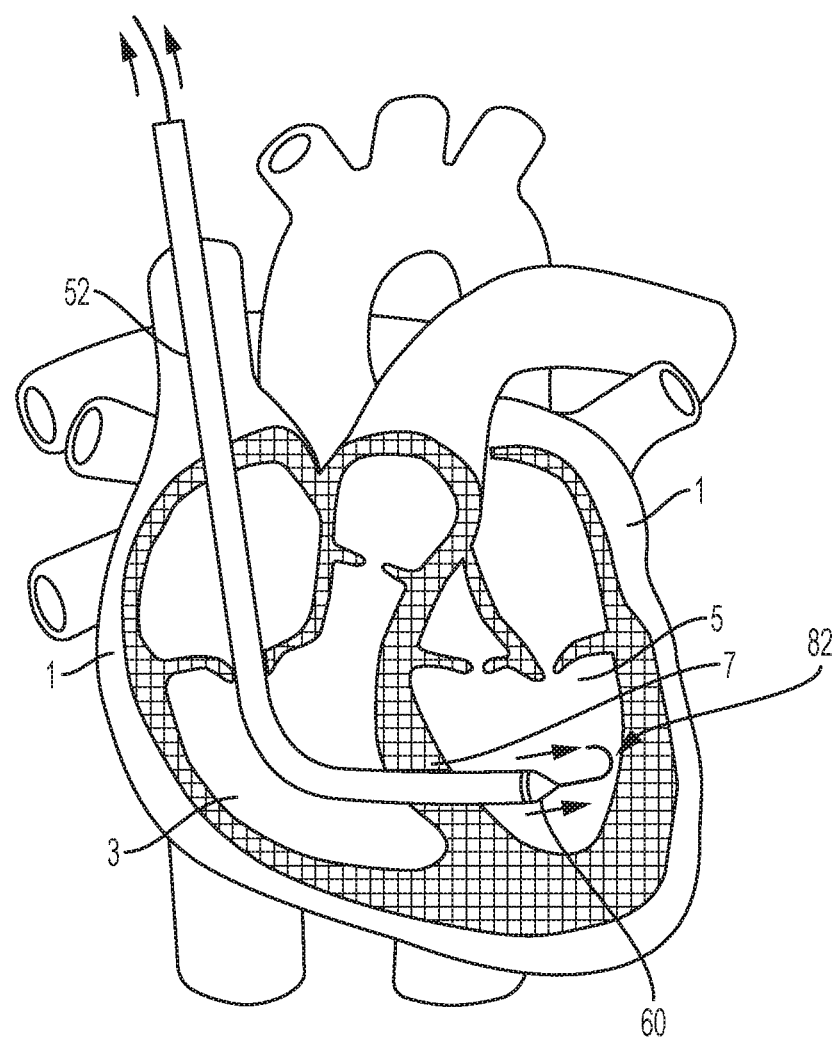
FIG. 29 is a perspective view of the interventricular tether system of FIG. 24, in which the delivery guide of the system has crossed the septum and entered the left ventricle.
Figure 30:
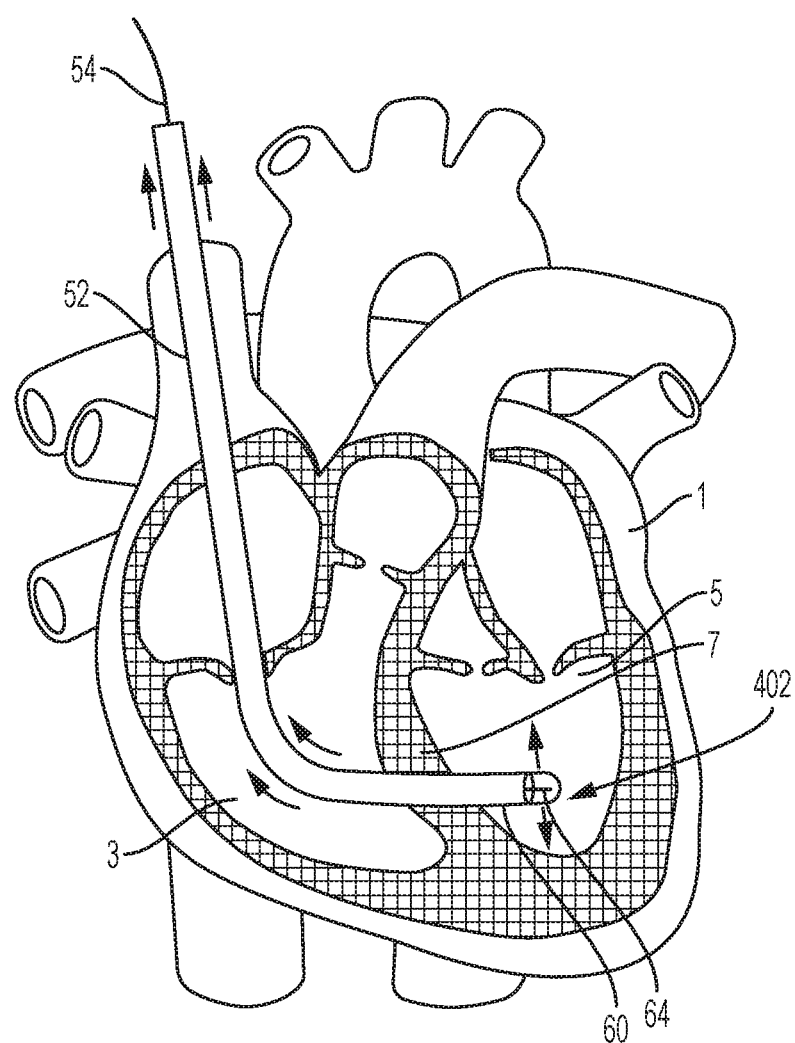
FIG. 30 is a perspective view of the interventricular tether system of FIG. 24, in which an anchor of the system is being positioned in the left ventricle.

In another aspect, illustrated in FIGS. 28 and 29, the anchor delivery guide 52 is inserted over the J-wire 82 until the tip 60 at the distal end 56 of the anchor delivery guide is positioned at or adjacent an anchoring site 416 in the left ventricle 5. The anchor delivery rod 54 is inserted through the inner guide lumen of the anchor delivery guide 52 until the distal end 64 of the anchor delivery rod is positioned in the left ventricle, illustrated in FIG. 30.

Figure 31:
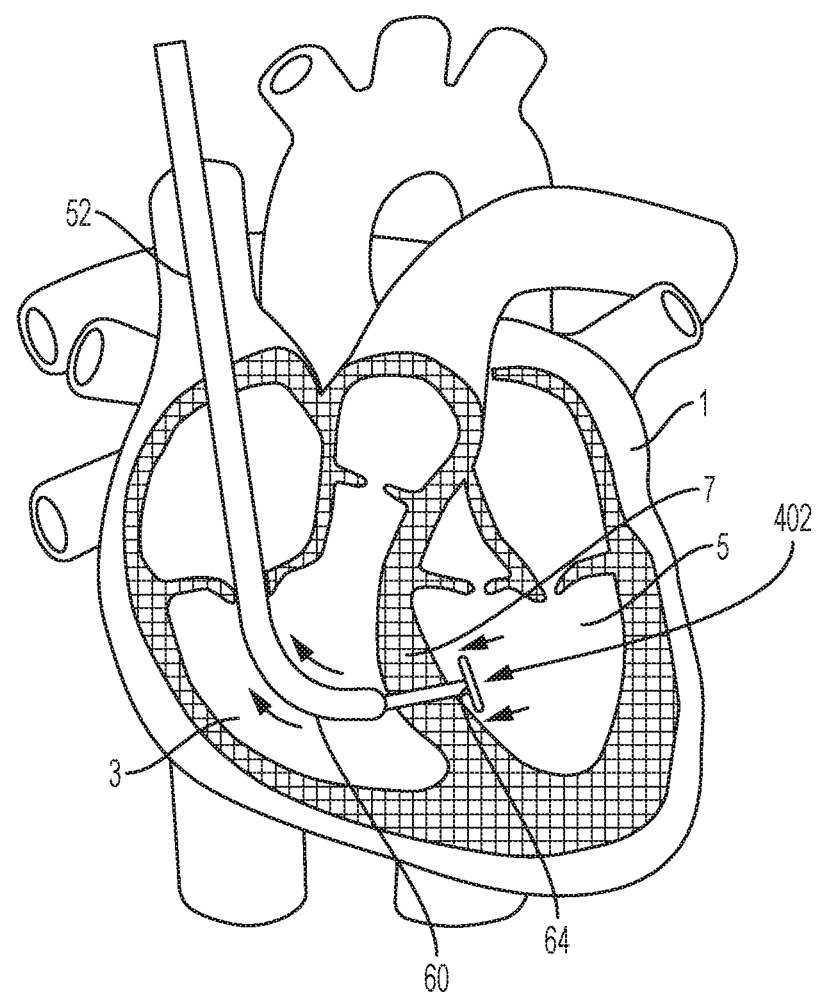
FIG. 31 is a perspective view of the interventricular tether system of FIG. 24, in which an anchor of the system has been deployed in the left ventricle.
Figure 32:
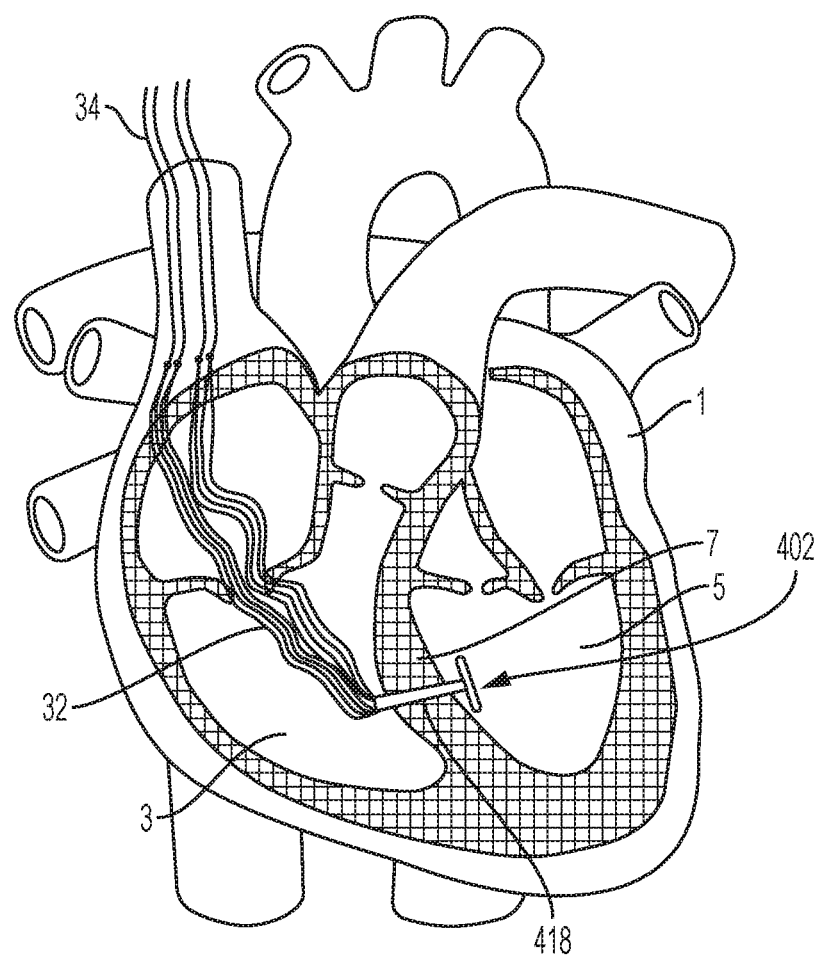
FIG. 32 is a perspective view of the interventricular tether system of FIG. 24, in which an anchor of the system has been deployed in the left ventricle and delivery devices of the system have been retracted.

The anchor 402 of the interventricular tether system 400 is coupled to the distal end 64 of the anchor delivery rod 54. In one aspect, the anchor is a self-expanding anchor (that is, the anchor is compressible so that it fits through the inner guide lumen of the anchor delivery guide 52). As illustrated in FIGS. 31 and 32, when the anchor 402 positioned on the distal end of the anchor delivery rod reaches the left ventricle 5, the anchor exits the inner guide lumen of the anchor delivery guide and expand to its full size, thereby locking the anchor 402 in place. As illustrated in FIG. 32, a right ventricle portion 418 of the anchor extends through the septum 7 and into the right ventricle 3.

In one aspect, the at least one cord 32 is coupled to the right ventricle portion 418 of the anchor 402 prior to deployment in the left ventricle 3. For example, the cord is coupled to the anchor such that the cord is positioned in the inner lumen of the anchor delivery rod 54. Thus, when the anchor delivery rod is removed from the heart 1, as illustrated in FIG. 32, the cord extends from the right ventricle portion of the anchor 402 through the tricuspid annulus. In this aspect then, the valve 12, detachable locks 126, 226 and the like is coupled to the cord 32 as previously described. It is within the scope of the present invention, however, for the anchor to be untethered or uncoupled from the valve upon insertion.

In another aspect, the interventricular anchor 402 is a screw, similar to anchor screw 28, or a fixation mechanism composed of, but not limited to, nitinol, stainless steel, cobalt-chromium, or titanium alloys, in the shape of barbs, hooks, prongs. This type of interventricular anchor could be delivered by the anchor delivery rod 54 via an anchor delivery guide 52.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A medical assembly for minimally invasively implanting a valve in the heart at a valve deployment site comprising:
   a valve configured for endovascular introduction and implantation and configured and sized to replace a native heart valve;
   an anchor configured and sized for endovascular introduction for anchoring to an anchoring site on an intracardiac wall;
   a tether assembly including at least one cord connected to said anchor and said valve for operatively connecting said valve and said anchor;
   a removable anchor delivery system for introducing said anchor and tether assembly endovascularly; and
   a removable valve delivery system for positioning and sealing the valve.

2. The medical assembly according to claim 1 wherein said anchor comprises:
   an anchor cap having a proximal and distal end; and
   an anchor screw extending from said anchor cap distal end and being configured to securely attach said anchor cap to the intracardiac wall at said anchoring site.

3. The medical assembly according to claim 2 wherein said tether assembly further comprises at least one suture extending from a proximal end of said at least one cord and a distal end of said at least one cord is connected to said proximal end of said anchor cap.

4. The medical assembly according to claim 3 wherein said tether comprises at least two of said cords extending from the proximal end of said anchor cap and wherein said tether comprises at least two of said sutures each extending from the proximal end of a respective one of said at least two cords.

5. The medical assembly according to claim 2 wherein said tether assembly comprises at least two of said cords extending from the proximal end of said anchor cap.

6. The medical assembly according to claim 2 wherein said removable anchor delivery system comprises an anchor delivery guide defining a longitudinally extending lumen and said anchor is removably received within said delivery guide lumen.

7. The medical assembly according to claim 6 wherein said removable anchor delivery system further comprises an anchor delivery rod removably positioned within said delivery guide lumen and configured for cooperation with said anchor.

8. The medical assembly according to claim 7 wherein said anchor delivery rod has a distal end having a first configuration and said anchor cap proximal end has a second configuration wherein said first and second configurations are mating configurations wherein rotational forces applied to said anchor delivery rod applies rotational forces to said anchor cap.

9. The medical assembly according to claim 7 wherein at least a portion of said tether assembly selectively extends within a rod lumen defined by said anchor delivery rod.

10. The medical assembly according to claim 9 wherein said at least one cord of said tether assembly selectively extends within said rod lumen.

11. The medical assembly according to claim 7 wherein at least a portion of said delivery rod is flexible.

12. The medical assembly according to claim 6 wherein said anchor delivery system further comprises a sheath removably coupled to and in fluid communication with the anchor delivery guide.

13. The medical assembly according to claim 6 wherein said tether assembly further comprises at least one suture extending from a proximal end of said at least one cord and a portion of said at least one suture extends within said delivery guide lumen and a proximal portion of said at least one suture extends from a proximal end of said delivery guide lumen.

14. The medical assembly according to claim 1 further comprising a J-wire for introducing said anchor delivery system.

15. The medical assembly according to claim 1 wherein said removable valve delivery system comprises a valve delivery guide defining an inner guide lumen and having a proximal and distal end, said valve delivery guide configured for receipt of said valve and a portion of said tether assembly.

16. The medical assembly according to claim 15 further comprises at least one suture extending from a proximal end of said at least one cord and said at least one cord is connected to said anchor and wherein said at least one of said suture and said at least one cord selectively extend through said inner guide lumen and cooperate with said valve, and said at least one suture extends beyond the inner guide lumen proximal end.

17. The medical assembly according to claim 16 wherein said valve defines an aperture and said at least one suture, selectively, extends through said valve aperture and said valve delivery guide further comprises at least one positioning rod defining a central lumen for selectively receiving said at least one suture wherein said positioning rod is positioned proximal to said valve, along said at least one suture and said at least one cord and cooperates with an upper surface of said valve to position said valve.

18. The medical assembly according to claim 17 wherein said removable valve delivery system comprises a valve deployment knob defining a central channel in fluid communication with said inner guide lumen and said positioning rod extends through said valve deployment knob central channel.

19. The medical assembly according to claim 17 wherein said tether assembly comprising said at least one cords comprises at least two cords, each extending from the proximal end of said anchor cap, said tether assembly comprising said at least one sutures comprises at least two of said at least one sutures, each extending from the proximal end of a respective one of said at least two cords, and said valve delivery system comprising said at least one positioning rods comprises two of said at least one positioning rods, each for selectively receiving a respective one of said at least two cords and one of said at least two sutures.

20. The medical assembly according to claim 15 wherein said removable valve delivery system comprises a valve deployment knob defining a central channel in fluid communication with said inner guide lumen wherein said valve deployment knob is operatively connected to said valve delivery guide wherein rotation of said deployment knob selectively extends and retracts said valve delivery guide within said delivery knob.

21. The medical assembly according to claim 15 wherein a distal portion of said valve delivery guide is flexible.

22. The medical assembly according to claim 15 wherein said valve delivery system further comprises a nosecone positioned on a distal end of said valve delivery guide and configured to guide the valve through the valve delivery guide to the valve deployment site.

* * * * *